United States Patent
Wolkowitz et al.

(10) Patent No.: US 9,732,386 B2
(45) Date of Patent: Aug. 15, 2017

(54) CELL AGING AS A UNIQUE BIOMARKER OF MAJOR DEPRESSION

(75) Inventors: Owen M. Wolkowitz, Palo Alto, CA (US); Synthia H. Mellon, San Francisco, CA (US); Elissa S. Epel, San Francisco, CA (US); Jue Lin, Foster City, CA (US); Elizabeth H. Blackburn, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 175 days.

(21) Appl. No.: 13/703,881

(22) PCT Filed: Jun. 24, 2011

(86) PCT No.: PCT/US2011/041909
§ 371 (c)(1),
(2), (4) Date: Jun. 12, 2013

(87) PCT Pub. No.: WO2011/163639
PCT Pub. Date: Dec. 29, 2011

(65) Prior Publication Data
US 2013/0289126 A1    Oct. 31, 2013

Related U.S. Application Data

(60) Provisional application No. 61/358,795, filed on Jun. 25, 2010.

(51) Int. Cl.
C12Q 1/68    (2006.01)
A61K 31/135    (2006.01)
C07H 21/02    (2006.01)

(52) U.S. Cl.
CPC .......... *C12Q 1/6883* (2013.01); *A61K 31/135* (2013.01); *C12Q 2600/156* (2013.01)

(58) Field of Classification Search
CPC  C12Q 1/686; C12Q 2521/113; C12Q 1/6883; C12Q 2600/156
See application file for complete search history.

(56) References Cited

PUBLICATIONS

Aubert, G. et al., Mut. Res., vol. 730, pp. 59-67 (2012).*
Zhou, X. et al., Chem. Soc. Rev., vol. 41, pp. 4643-4656 (2012).*
Needham, B.L. et al., Mol. Psychiatry, pp. 1-9 (Sep. 2, 2014).*
Soeiro-de-Souza, M.G. et al., Eur. Neuropsychopharm., vol. 24, pp. 1139-1143 (2014).*
Lin, K-W. et al., J. Cell. Mol. Med., vol. 9, pp. 977-989 (2005).*
Fajkus, J., Clin. Chim. Acta, vol. 371, pp. 25-31 (2006).*
Calado et al., N Engl J Med, 361(24):2353-2365 (2009).
Cawthon, Nucleic Acids Res., 30(10):e47 (2002).
Damjanovic et al., "Accelerated telomere erosion is associated with a declining immune function of caregivers of Alzheimer's disease patients," Journal of Immunology, 2007, vol. 179, pp. 4249-4254.
Duman et al., "A Molecular and Cellular Theory of Depression," Archives of General Psychiatry, 54(7):597-606 (Jul. 1997).
Epel et al., "Dynamics of telomerase activity in response to acute psychological stress," Brain Behav Immun., May 2010, 24(4):531-9. doi: 10.1016/j.bbi.2009.11.018. Epub Dec. 16, 2009.
Epel, Hormones (Athens), 8(1):7-22 (2009).
Epel et al., Proceedings Natl. Acad. of Sci USA, 101(49):17312-17315 (2004).
Epel et al., "Cell aging in relation to stress arousal and cardiovascular disease risk factors," Psychoneuroendocrinology, 31(3):277-287 (2006).
Lung et al., "Genetic pathway of major depressive disorder in shortening telomeric length," Psychiatric Genet., 17(3):195-199 (2007).
Manji et al., "Signal Transduction and Genes-to-Behaviors Pathways in Psychiatric Diseases," SciSTKE, 207:pe49 (2003).
O'Donovan et al., "Pessimism correlates with Leukocyte telomere shortness and elevated interleukin-6 in post-menopausal women," Brain, behavior, and immunity, 23(4):446-449 (2009).
Simon et al, "Telomere shortening and mood disorders: preliminary support for a chronic stress model of accelerated aging," Biol. Psychiatry, 2006, vol. 60, pp. 432-435.
Torpey et al., "Chronic Depression: Update on the Classification and Treatment," Current Psychiatry Reports, 10:456-464 (2008).
Wolkowitz et al., "Depression gets old fast: do stress and depression accelerate cell aging?" Depress Anxiety, 2010, 27(4):327-328, doi: 10.1002/da.20686.
Wolkowitz et al., "When blue turns to grey: do stress and depression accelerate cell aging?" World J. Biol. Psychiatry, 2008, 9(1):2-5; doi: 10.1080/15622970701875601.

* cited by examiner

*Primary Examiner* — Teresa Strzelecka
(74) *Attorney, Agent, or Firm* — Kilpatrick Townsend & Stockton LLP

(57) ABSTRACT

The present invention provides methods of determining whether a subject is a suitable candidate for an anti-depressant treatment to alleviate a mood disorder by measuring telomere length and telomerase activity. The present invention also provides methods of assessing the efficacy of an anti-depressant treatment to alleviate a mood disorder and of predicting whether a subject is at risk of developing depression.

7 Claims, 12 Drawing Sheets

CELL AGING AS A UNIQUE BIOMARKER OF MAJOR DEPRESSION

CROSS-REFERENCES TO RELATED APPLICATIONS

This application is a U.S. national stage entry under 35 U.S.C. §371 of PCT/US2011/041909, filed Jun. 24, 2011, which claims priority to U.S. Provisional Application Ser. No. 61/358,795, filed on Jun. 25, 2010, the contents of each of which are incorporated herein by reference in its entirety.

STATEMENT AS TO RIGHTS TO INVENTIONS MADE UNDER FEDERALLY SPONSORED RESEARCH AND DEVELOPMENT

This invention was made with Government Support under grant no. UL1 RR024131 awarded by the National Institutes of Health. The Government has certain rights in the invention.

BACKGROUND OF THE INVENTION

Clinical depression, including Major Depressive Disorder ("MDD"), is a significant public health problem. Major depression is associated with a significantly increased risk of developing serious medical illnesses such as diabetes, cardiovascular disease, immune impairments ("immunosenescence"), stroke, dementia, osteoporosis, diabetes and metabolic syndrome, and of dying significantly earlier (even after accounting for socio-demographic factors, suicide and risk factors such as smoking, alcohol and physical illness). See, e.g., Brown E S, Varghese F P, McEwen B S, *Biol Psychiatry*, 55(1):1-9 (2004); Musselman D L, Evans D L, Nemeroff C B, *Archives of General Psychiatry*, 55(7):580-592 (1998); McCusker J et al., *Gen Hosp Psychiatry*, 29(4):340-348 (2007); Irwin M R, Miller A H, *Brain, Behavior, and Immunity*, 21(4):374-383 (2007); Godbout J P, Johnson R W, *Neurologic Clinics*, 24(3):521-538 (2006)), (Arfken C L, Lichtenberg P A, Tancer M E, *The Journals of Gerontology*, 54(3):M152-156 (1999); Schulz R et al., *Archives of Internal Medicine*, 160(12):1761-1768 (2000); Evans D L et al., *Biol Psychiatry*, 58(3):175-189 (2005); Gump B B et al., *Stroke*, 36(1):98-102 (2005); Rapp M A et al., *Am J Geriatr Psychiatry*, 16(10):844-852 (2008)).

Intensive research has been aimed at characterizing the pathophysiology of major depression on a cellular and molecular level. See, e.g., Duman R S et al., *Archives of General Psychiatry*, 54(7):597-606 (July 1997); Manji H K and Gottesman, II, *Sci STKE*, 207:pe49 (2003). However, there is currently no established biological or clinical test that can predict who is likely to develop depression. Additionally, although antidepressant medications and/or psychotherapy can be efficacious in treating depression, it is often inadequately treated and many patients fail to respond or continue to experience residual symptoms after treatment. Torpey D C and Klein D N, *Current Psychiatry Reports*, 10:458-464 (2008).

Therefore, there is a need in the field to develop methods for predicting whether a person is likely to develop depression, or if a person has been diagnosed with depression, whether that person is likely to respond to an anti-depressant treatment. The present invention addresses this need and others.

BRIEF SUMMARY OF THE INVENTION

In one aspect, the present invention provides a method of determining whether a subject is a suitable candidate for an anti-depressant treatment to alleviate a mood disorder, the method comprising the steps of measuring telomerase activity in a sample from the subject prior to administration of the anti-depressant treatment; and determining whether the telomerase activity from the sample is lower than a control value, wherein telomerase activity lower than the control value indicates that the subject is likely to respond to the anti-depressant treatment. In one embodiment, the control value is 9.5 units/10,000 cells. In one embodiment, the method further comprises administering the anti-depressant treatment to the subject.

In another aspect, the present invention provides a method of determining whether a subject is a suitable candidate for an anti-depressant treatment to alleviate a mood disorder, the method comprising the steps of measuring telomere length and telomerase activity in a sample from the subject prior to administration of the anti-depressant treatment; and determining the ratio of telomere length to telomerase activity in the sample, wherein a ratio of telomere length to telomerase activity in the sample that is higher than a control value indicates that the subject is a suitable candidate for the anti-depressant treatment. In one embodiment, the method further comprises administering the anti-depressant treatment to the subject. In one embodiment, the method further comprises the step of determining that the telomerase activity in the sample from the subject prior to administration of the anti-depressant treatment is lower than a baseline value, indicating that the subject is more likely to respond to the anti-depressant treatment than a subject whose telomerase activity is higher than the baseline value.

In yet another aspect, the present invention provides a method of assessing the efficacy of anti-depressant treatment to alleviate a mood disorder, the method comprising the steps of measuring telomerase activity in a first sample from the subject taken prior to administration of the anti-depressant treatment; measuring telomerase activity in a second sample from the subject taken during administration of the anti-depressant treatment; and determining the change in telomerase activity in the second sample as compared to the first sample, wherein an increase in telomerase activity in the second sample as compared to the first sample or a decrease in telomerase activity in the second sample of no more than 2.5 units/10,000 cells as compared to the first sample indicates that the subject is responding to the anti-depressant treatment. In one embodiment, the increase in telomerase activity in the second sample as compared to the first sample or the decrease in telomerase activity in the second sample of no more than 2.5 units/10,000 cells as compared to the first sample predicts a decreased likelihood of relapse of the mood disorder in the subject. In one embodiment, the method further comprises the step of determining that the decrease in telomerase activity in the second sample as compared to the first sample is more than 2.5 units/10,000 cells, thereby indicating that the subject is not likely to respond to the anti-depressant treatment.

In still another aspect, the present invention provides a method of predicting whether a subject is at risk of developing depression, the method comprising the steps of measuring telomere length and telomerase activity in a sample from the subject; and determining whether the telomere length from the sample is shorter than a first control value and whether the telomerase activity from the sample is lower than a second control value, wherein a combination of telomere length shorter than the first control value and telomerase activity lower than the second control value indicates that the subject is at risk of developing depression. In one embodiment, the combination of telomere length shorter than the first control value and telomerase activity lower than the second control value indicates that the subject is at risk of developing depression for at least one year from the time the sample is taken from the subject.

In yet another aspect, the present invention provides a method of predicting whether a subject is at risk of developing depression, the method comprising the steps of measuring telomere length and telomerase activity in a sample from the subject; and determining whether the telomere length from the sample is shorter than a first control value and whether the telomerase activity from the sample is higher than a second control value, wherein a combination of telomere length shorter than the first control value and telomerase activity higher than the second control value indicates that the subject is at risk of developing depression.

In one embodiment, the sample is from blood, lymph, saliva, cerebrospinal fluid, urine, tissue biopsy, or hair follicles. In one embodiment, the sample is from whole blood or peripheral blood mononuclear or granulocyte cells.

In one embodiment, the mood disorder is a depressive disorder or an anxiety disorder. In one embodiment, the mood disorder is selected from the group consisting of depression, Major Depressive Disorder, anxiety disorder, dysthymia, Obsessive-Compulsive Disorder, panic, social phobia, bipolar disorder, dysphoria, cyclothymia, and Post-Traumatic Stress Disorder. In one embodiment, the mood disorder is Major Depressive Disorder.

In one embodiment, the anti-depressant treatment comprises anti-depressant medication or psychotherapy.

DETAILED DESCRIPTION OF THE INVENTION

I. Introduction

Figure 1:
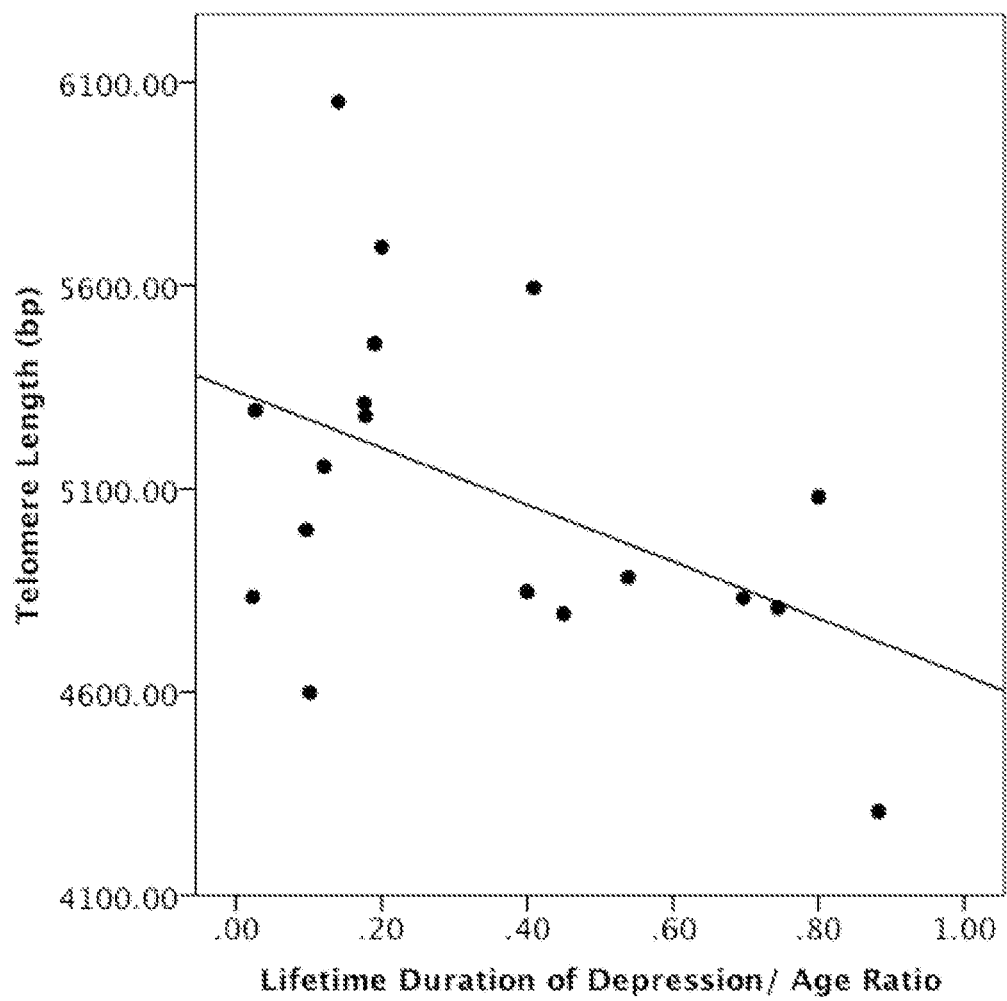
FIG. 1. Relationship between cumulative lifetime duration of depression and leukocyte telomere length (in base pairs, bp). To correct for age, which is also associated with telomere shortening, lifetime depression is shown as a ratio with age (with a theoretical minimum of zero for no lifetime depression and one for a complete lifetime of depression).

Major depression has been likened to a state of "accelerated aging," with an increased incidence of aging-related illnesses. See Brown E S, Varghese F P, McEwen B S, *Biol Psychiatry*, 55(1):1-9 (2004); Evans D L et al., *Biol Psychiatry*, 58(3):175-189 (2005); Heuser I, *Maturitas*, 41 Suppl 1:S19-23 (2002); Lupien S J et al., *Rev Neurosci*, 10(2):117-139 (1999); McEwen B S, Magarinos A M, *Human Psychopharmacol Clin Exp.*, 16:S7-S19 (2001); Sapolsky R M, *Biol Psychiatry*, 48(8):755-765 (2000); Horrobin D F, Bennett C N, *Prostaglandins Leukot Essent Fatty Acids*, 60(4):217-234 (1999); Kiecolt-Glaser J K, Glaser R, *Journal of Psychosomatic Research*, 53(4):873-876 (2002); Licinio J, Wong M L, *Mol Psychiatry*, 4(4):317-327 (1999); Andersen K, Lolk et al., Epidemiology, 16(2):233-238 (2005); Chodosh J et al., *J Am Geriatr Psychiatry*, 55(8):1260-1268 (2007); Speck C E et al., *Epidemiology*, 6(4):366-369 (1995); Kessing L V, Andersen P K, *J Neurol Neurosurg Psychiatry*,75(12):1662-1666 (2004); McIntyre R S et al., *Ann Clin Psychiatry*, 19(4):257-264 (2007). Recent studies have found prematurely shortened leukocyte telomeres in individuals with certain serious diseases associated with aging (many of which are seen with higher prevalence in depressed populations, e.g., cardiovascular disease, stroke, dementia, osteoporosis, metabolic syndrome and diabetes (Epel E S, *Hormones (Athens)*, 8(1):7-22 (2009); Epel E S et al., *Psychoneuroendocrinology*, 31(3):277-287 (2006); Serrano A L and Andres V., *Circ Res*, 94(5):575-584 (2004); Samani N J et al.,*Lancet*, 358(9280):472-473 (2001); Huzen J et al., *Front Biosci*, 15:35-45 (2010); Grodstein F et al., *PloS one*, 3(2):e1590 (2008); Fuster J J and Andres V., *Circ Res*, 99(11):1167-1180 (2006); Farzaneh-Far R et al., *Arteriosclerosis, Thrombosis, and Vascular Biology*, 28(7):1379-1384 (2008); Cawthon R M et al., *Lancet*, 361(9355):393-395 (2003); Brouilette S W et al., *Lancet*, 369(9556):107-114 (2007); Aviv A., *The Journals of Gerontology*, 61(8):871-873 (2006); Adaikalakoteswari A et al., *Diabet Med*, 22(9):1151-1156 (2005); Valdes A M et al., *Osteoporos Int*, 18(9):1203-1210 (2007); Epel E S et al., *Aging* 2009 published on line: Dec. 19, 2008, 1(1):81-88)). Additionally, it has recently been shown that depression, as well as chronic stress, is associated with shortened whole blood telomere length (Epel E S et al., *Proc. Natl. Acad. of Sci. USA*, 101(49):17312-17315 (2004); (Simon N M et al., *Biol Psychiatry*, 60(5):432-435 (2006)).

Telomeres are nucleoprotein complexes at the ends of linear DNA strands and chromosomes that stabilize the linear DNA strands and chromosomes and protect the linear DNA strands and chromosomes from damage. In mitotic cells, telomeres can shorten with each division, unless this can be reversed by the telomere-lengthening enzyme, telomerase. When telomeres shorten to a critical length, cells become susceptible to senescence and apoptosis (Blackburn E H., *Nature*, 408(6808):53-56 (2000); Blackburn E H et al., *Nat Med*, 12(10):1133-1138 (2006); Beyne-Rauzy O et al., *Blood*, 106(9):3200-3205 (2005); Effros R B, *The Journals of Gerontology*, 64(5):511-515 (2009); Calado R T and Young N S, *N Engl J Med*, 361(24):2353-2365 (2009)). Even in somatic cells, telomere shortening has been associated with cytotoxic stressors such as oxidative stress, which preferentially damages telomeric DNA compared with non-telomeric DNA, and chronic inflammation (De Meyer T et al., *Front Biosci.*, 13:2960-2970 (2008); Houben J M et al., *Free Radical Biology & Medicine*, 44(3):235-246 (2008); von Zglinicki T, *Trends Biochem Sci.*, 27(7):339-344 (2002); Aviv A, *Sci Aging Knowledge Environ.*, 2004(51):pe43 (2004)). Such telomere shortening also increases cellular susceptibility to apoptosis and death (Zhang P, Dilley C, Mattson M P, *Neuroscience*, 145(4):1439-1448 (2007)).

Telomere length is determined by the balance between telomere shortening stimuli (e.g., mitotic divisions and exposure to inflammation and oxidation) and telomere lengthening or reparative stimuli (Blackburn E H., *Nature*, 408(6808):53-56 (2000); Blackburn E H et al., *Nat Med*, 12(10):1133-1138 (2006); Calado R T and Young N S, *N Engl J Med*, 361(24):2353-2365 (2009); Epel E S et al., *Proceedings of the National Academy of Sciences of the United States of America*, 101(49):17312-17315 (2004); von Zglinicki T and Martin-Ruiz C M, *Current Molecular Medicine*, 5(2):197-203 (2005); von Zglinicki T, *Trends Biochem Sci*, 27(7):339-344 (2002)). A major enzyme responsible for protecting, repairing and lengthening telomeres is telomerase, a ribonucleic enzyme that rebuilds telomere length and maintains cellular viability, although it also has important non-telomeric actions, such as regulating the transcription of growth factors and stimulating cell growth in adverse conditions (Calado R T and Young N S, *N Engl J Med*, 361(24):2353-2365 (2009); Mattson M P et al., *Mechanisms of Ageing and Development*, 122(7):659-671 (2001); Gorbunova V and Seluanov A, *Cell Cycle*, 2(6):534-537 (2003); Zhu H et al., *J Neurochem*, 75(1):117-124 (2000); Calado R T and Chen J., *Bioessays*, 28(2):109-112 (2006); Geserick C and Blasco M A., *Mechanisms of Ageing and Development*, 127(6):579-583 (2006); Sung Y H et al., *Mol Cells*, 19(3):303-309 (2005); Kang H J et al., *J Neurosci*, 24(6):1280-1287 (2004)).

In a study associating telomere length with chronic stress, healthy but chronically stressed women (including maternal caregivers of chronically ill children) showed significantly shorter leukocyte telomere length compared to controls, and telomere length was inversely correlated with the severity of perceived stress as well as with the chronicity of caregiving (viz., women with greater cumulative duration of caregiving stress had shorter telomeres). The difference in mean telomere base pairs (bp) between the two groups suggested approximately 9-17 years of accelerated biological aging in the stressed, compared to the non-stressed, women (Epel E S et al., *Proc. Natl. Acad. of Sci. USA*, 101(49):17312-17315 (2004)). In a study examining telomere length and major depression, it was found that depressed subjects had significantly shortened leukocyte telomere length compared to controls, with an estimated acceleration of biological cell aging of over 10 years (average telomere shortening=660 bp). That study had certain limitations, however, including the study of a mixed group of mood disordered subjects (including those with bipolar illness), the use of historical rather than prospectively recruited controls, the lack of structured diagnostic evaluations of the controls, the lack of investigation of possible biochemical mediators of telomere shortening, and the study of a very chronically ill population (average lifetime duration of illness=31.8±11.2 [SD] years) (Simon N M et al., *Biol Psychiatry*, 60(5):432-435 (2006)). In the only other study known to have examined leukocyte telomere shortening in depression, shortened telomeres were also found, although that study did not describe the chronicity of depression in their sample (Lung F W et al., *Psychiatr Genet.*, 17(3):195-199 (2007)).

Far fewer studies have characterized telomerase activity in these conditions, and no studies have yet characterized telomerase activity in individuals with major depression. Determination of telomerase activity is critical to understanding the reported shortening of leukocyte telomeres in depression and to assess whether the reduced telomere length is due to increased shortening, decreased repair, or both. Adding further complexity to this issue, both high and low telomerase activity can be associated with shortened telomeres. Low telomerase activity could be causally associated with shortened telomeres by impairing the repair of damaged or shortened telomeres (Effros R B, *The Journals of Gerontology*, 64(5):511-515 (2009); Rudolph K L et al., *Cell*, 96(5):701-712 (1999); Effros R B, *Experimental Gerontology* (2006)). Conversely, unusually high telomerase activity could represent a failed compensatory attempt to maintain telomere length in the face of cellular stress (e.g., increased inflammation and oxidation) (Damjanovic A K et al., *J Immunol*, 179(6):4249-4254 (2007); Zhang J et al., *Cogn Behav Neurol*, 16(3):170-176 (2003)). Further, since telomerase has a number of poorly understood non-telomeric functions (Mattson M P et al., *Mechanisms of Ageing and Development*, 122(7):659-671 (2001); Gorbunova V and Seluanov A, *Cell Cycle*, 2(6):534-537 (2003); Zhu H et al., *J Neurochem*, 75(1):117-124 (2000); Calado R T and Chen J., *Bioessays*, 28(2):109-112 (2006); Geserick C and Blasco M A., *Mechanisms of Ageing and Development*, 127(6):579-583 (2006); Sung Y H et al., *Mol Cells*, 19(3): 303-309 (2005)), abnormal telomerase activity in depression could result in unanticipated consequences. Finally, depending upon its effects, alterations in telomerase activity could influence treatment responsiveness in depressed individuals, and antidepressants, in turn, could alter telomerase activity as part of their mechanism of action.

The present invention is based in part on the discoveries that total lifetime days of depression are significantly and inversely correlated with telomere length, and that telomerase activity is significantly higher in untreated depressed individuals compared to healthy matched controls. These findings suggest novel methods for predicting the risk of or diagnosing depression by measuring and evaluating telomere length and telomerase activity, as provided herein by the present invention.

The present invention is also based in part on the discovery that pre-treatment levels of telomerase activity, and/or pre-treatment ratios of telomere length to telomerase activity, predict response to anti-depressant treatment. Specifically, depressed individuals with relatively lower baseline (pre-medication) telomerase activities, and those whose telomerase activities increased the most with anti-depressant treatment, showed the greatest benefit from anti-depressant treatment. These findings therefore suggest novel methods for predicting whether an individual is a suitable candidate for anti-depressant treatment, and/or predicting whether an individual is likely to respond to anti-depressant treatment, by measuring and evaluating telomerase activity and/or the ratio of telomere length to telomerase activity, as provided herein by the present invention.

II. Definitions

As used herein, the following terms have the meanings ascribed to them unless specified otherwise.

As used herein, the term "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., *Diagnostic and Statistical Manual of Mental Disorders, Fourth Edition*, Washington, D.C., American Psychiatric Association (1994) ("DSM IV").

As used herein, the terms "Major Depressive Disorder" or "major depression disorder" refer to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed; decreased energy, fatigue, or being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physician symptoms that do not respond to treatment, such as headaches, digestive disorders, and chronic pain. Various subtypes of major depressive disorder are described in, e.g., DSM IV.

As used herein, the term "bipolar disorder" refers to a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

As used herein, the terms "anti-depressant treatment" or "treatment" refers to any agent or any form of psychological treatment or psychotherapy typically used to treat or alleviate clinical depression. Anti-depressant agents include compounds of different classes including, for example, selective serotonin reuptake inhibitors (e.g., sertraline or escitalopram), tricyclic antidepressants (e.g., desipramine), and dopamine reuptake inhibitors (e.g, bupropion). Typically, anti-depressants of different classes exert their therapeutic effects via different biochemical pathways. Often these biochemical pathways overlap or intersect. Additional diseases or disorders often treated or alleviated with antidepressants include chronic pain and anxiety disorders. Psychotherapy includes any of various means involving communication between a patient and a therapist. Anti-depressant treatment may also include a combination of anti-depressant agents and psychotherapy.

As used herein, the term "telomere" refers to a functional nucleoprotein complex at the ends of linear DNA strands and chromosomes that stabilizes the linear DNA strands and chromosomes and protect against instability-promoting events such as degradation of the terminal regions of chromosomes, fusion of a telomere, either with another telomere or with a broken DNA end, or inappropriate recombination. Telomeres are composed of telomeric DNA, comprising tandemly repeated nucleotide sequences (e.g., the telomere sequence (TTAGGG)n is a conserved sequence, with "n" referring to the number of repeats of the sequence), as well as telomere-binding proteins which bind to the tandem DNA repeats. Collectively, the tandem DNA repeats and bound telomere-binding proteins form a telomere complex that caps the ends of linear DNA strands and chromosomes to stabilize and protect the linear DNA strands and chromosomes from damage. "Telomere length" can refer to either the number of nucleotides comprising the telomeric DNA or the number of telomere repeats. Telomere length is determined by the balance between telomere shortening stimuli (e.g., mitotic divisions and exposure to inflammation and oxidation) and telomere lengthening stimuli (e.g., enzymes such as telomerase). Telomere length can be quantified by any of a number of assays, including but not limited to PCR (e.g., quantitative PCR), nucleic acid hybridization techniques (e.g., telomere restriction fragment (TRF) analysis by Southern blot), and fluorescent in situ hybridization (e.g., quantitative FISH or flow cytometry FISH). Telomere length may be "shorter" or "longer" in a sample taken from a subject (e.g., a subject having a mood disorder or a subject receiving anti-depressant treatment to alleviate a mood disorder) relative to a "control value," such as the telomere length in a sample taken from a control subject (e.g., a subject who does not have a mood disorder) or the mean telomere length among a population of subjects (e.g., a group of subjects all receiving anti-depressant treatment to alleviate a mood disorder). For determining whether telomere length in a sample from a subject is shorter or longer than a control value, the control sample (e.g., a sample taken from a subject who does not have a mood disorder) is assigned a relative value of 100%, or the mean telomere length is quantified for the population of subjects (e.g., a group of subjects all receiving anti-depressant treatment to alleviate a mood disorder) and the mean is assigned a relative activity value of 100%. Telomere length in a sample from a subject is shorter than a control value when the telomere length from the subject relative to the control is about 90%, about 85%, about 80%, about 75%, about 70%, about 65%, or about 60% or less. Telomere length in a sample from a subject is longer than a control value when the telomere length in the sample from the subject relative to the control is about 110%, about 120%, about 130%, about 140%, about 150%, about 175%, about 200%-500%, or about 1000%-3000% or greater.

As used herein, the term "telomerase" refers to a reverse transcriptase enzyme that rebuilds telomere length and maintains cellular viability. The telomerase enzyme comprises a protein component, called TERT (Telomerase Reverse Transcriptase) and an RNA component, called TER (Telomerase RNA). Telomerase functions by copying a short template sequence within the TER to synthesize the DNA sequence repeats (e.g., TTAGGG repeats in vertebrates) that are added to the 3' ends of telomeric DNA strands. "Telomerase activity" refers to the enzymatic activity of the telomerase to catalyze the addition of DNA sequence repeats to the ends of DNA. Telomerase activity can be quantified by any of a number of assays, including but not limited to telomeric repeat amplification protocol (TRAP), real-time quantitative TRAP, and immunoassay (e.g. ELISA assay that detects telomerase reaction product). Telomerase activity may be "lower" or "higher" in a sample taken from a subject (e.g., a subject having a mood disorder or a subject receiving anti-depressant treatment to alleviate a mood disorder) relative to a "control value," such as the amount of telomerase activity in a sample taken from a control subject (e.g., a subject who does not have a mood disorder) or the mean amount of telomerase activity among a population of subjects (e.g., a group of subjects all receiving anti-depressant treatment to alleviate a mood disorder). For determining whether telomerase activity in a sample taken from a subject is higher or lower than a control value, the control sample (e.g., a sample taken from a subject who does not have a mood disorder) is assigned a relative activity value of 100%, or the mean telomerase activity is quantified for the population of subjects (e.g., a group of subjects all receiving anti-depressant treatment to alleviate a mood disorder) and the mean is assigned a relative activity value of 100%. Telomerase activity in a sample taken from a subject is lower than a control value when the activity in the sample taken from the subject relative to the control value is about 90%, about 85%, about 80%, about 75%, about 70%, about 65%, or about 60% or less. Telomerase activity in a sample from a subject is higher than a control value when the activity in the sample taken from the subject relative to the control value is about 110%, about 120%, about 130%, about 140%, about 150%, about 175%, about 200%-500%, or about 1000%-3000% or greater.

Telomerase activity may also be assessed by determining "baseline" and/or "delta" or "changed" telomerase activity levels for a subject and comparing the subject's baseline and/or delta telomerase activity levels to a cutoff value. In some embodiments, a baseline telomerase activity level that indicates that a subject is likely to respond to anti-depressant treatment is less than about 9.0 units/10,000 cells or less than about 9.5 units/10,000 cells (e.g., less than about 9.0 units/10,000 cells, less than about 9.1 units/10,000 cells, less than about 9.2 units/10,000 cells, less than about 9.3 units/10,000 cells, less than about 9.4 units/10,000 cells, or less than about 9.5 units/10,000 cells). In some embodiments, a baseline telomerase activity level in a subject that is less than 9.5 units/10,000 cells and a delta telomerase activity level in the subject that is increased from the baseline, the same as the baseline, or decreased no more than 2 units from the subject's baseline level predicts response to anti-depressant treatment. As used herein, units are determined by measuring the telomerase activity in a cell of interest (e.g., PBMCs) and comparing to the telomerase activity in a control cell (e.g., 293T cells), as described herein in the Examples section. For example, telomerase activity in each of a cell of interest (PBMCs) and in a positive control (293Ts) can be quantified and normalized against an internal control band to yield a product/internal control value for each of the PBMC and 293T assays. The product/internal control value of the cell of interest (PBMCs) can be divided by the product/internal control value of the positive control (293Ts), then multiplied by 20 to yield the final telomerase activity, wherein 1 unit=the amount of product from one 293T cell/10,000 PBMCs. In some embodiments, "response" to anti-depressant treatment refers to at least a 50% improvement (i.e., decrease in depressive symptoms) relative to baseline. In some embodiments, a baseline telomerase activity level in a subject that is less than 9.0 units/10,000 cells and a delta telomerase activity level in the subject that is increased from the baseline, the same as the baseline, or decreased no more than 2.5 units from the subject's baseline level predicts remission of depression from anti-depressant treatment.

In some embodiments, both telomere length and telomerase activity may be measured in a subject (e.g., a subject having a mood disorder or a subject receiving anti-depressant treatment to alleviate a mood disorder) and a ratio of telomere length to telomerase activity may be generated and compared to a control value (e.g. a ratio of telomere length to telomerase activity in a sample taken from a subject who does not have a mood disorder). A ratio of telomere length to telomerase activity in a sample taken from a subject may be higher (e.g., about 10%, about 20%, about 30%, about 40%, about 50%, about 60%, about 70%, about 80%, or about 90% higher) or lower (e.g., about 10%, about 20%, about 30%, about 40%, about 50%, about 60%, about 70%, about 80%, or about 90% lower) than a control value.

As used herein, the terms "nucleic acid," "polynucleotide," and "oligonucleotide" refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, haplotypes, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

As used herein, the term "sample" includes extractions of nucleic acid such as DNA, sections of tissues such as biopsy and autopsy samples, and frozen sections taken for histological purposes. Such samples include blood and blood fractions or products (e.g., serum, buffy coat, plasma, platelets, red blood cells, peripheral blood mononuclear cells, and the like), sputum, cheek cells tissue, cultured cells (e.g., primary cultures, explants, and transformed cells), stool, urine, hair follicles, other biological fluids (e.g., lymph, saliva, prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish.

As used herein, the terms "therapeutically effective amount" or "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

III. Diagnostic and Prognostic Methods

The present invention provides methods of diagnosing a mood disorder (such as major depression or bipolar disorder) or a predisposition for developing a mood disorder. The present invention also provides methods of providing a prognosis for whether a subject is a suitable candidate for an anti-depressant treatment to alleviate a mood disorder and provides a method of assessing the efficacy of an anti-depressant treatment to alleviate a mood disorder.

Mood Disorders

The mood disorders which are contemplated by the present invention include such disorders as depression, Major Depression Disorder, anxiety disorder, dysthymia, Obsessive-Compulsive Disorder, panic, social phobia, bipolar disorder, dysphoria, cyclothymia, and Post-Traumatic Stress Disorder as set forth in the *Diagnostic and Statistical Manual of Mental Disorders, Fourth Edition* (American Psychiatric Association, DSM-IV, 4th Ed. 1994).

In any given 1-year period, 9.5 percent of the population, or about 18.8 million American adults, suffer from a depressive illness (Robins & Regier (Eds). *Psychiatric Disorders in America, The Epidemiologic Catchment Area Study*, 1990; New York: The Free Press). Depression often accompanies anxiety disorders (Regier et al., *British Journal of Psychiatry Supplement* 34: 24-8 (1998)) and, when it does, it needs to be treated as well. Symptoms of depression include feelings of sadness, hopelessness, changes in appetite or sleep, low energy, and difficulty concentrating. Most people with depression can be effectively treated with anti-depressant medications, certain types of psychotherapy, or a combination of both.

Depressive disorders are expressed in different forms:
Major depression is manifested by a combination of symptoms (see symptom list) that, for example, interfere with the ability to work, study, sleep, eat, and enjoy once pleasurable activities. Such a disabling episode of depression may occur only once but more commonly occurs several times in a lifetime.

Dysthymia, a less severe type of depression, involves long-term, chronic symptoms that do not disable, but keep one from functioning well or from feeling good. Many people with dysthymia also experience major depressive episodes at some time in their lives.

Bipolar disorder, also called manic-depressive disorder, is another type of depression. Not nearly as prevalent as other forms of depressive disorders, bipolar disorder is characterized by cycling mood changes: severe highs (mania) and lows (depression). Sometimes the mood switches are dramatic and rapid, but most often they are gradual. When in the depressed cycle, an individual can have any or all of the symptoms of a depressive disorder. When in the manic cycle, the individual may be overactive, overtalkative, and have a great deal of energy. Mania often affects thinking, judgment, and social behavior in ways that cause serious problems. For example, the individual in a manic phase may feel elated, and full of grand schemes. Mania, left untreated, may worsen to a psychotic state.

Major Depression Disorder (MDD) is characterized by clinically significant depressions of mood and impairment of functioning as its primary clinical manifestations. Its clinical manifestations and current treatment overlap the anxiety disorders including panic-agoraphobia syndrome, sever phobias, generalized anxiety disorder, social anxiety disorder, post-traumatic stress disorders and obsessive-compulsive disorder. Extremes of mood may be associated with psychosis, manifested as disordered or delusional thinking and perceptions, often congruent with the predominant mood. Symptoms of MDD include persistent sad, anxious, or "empty" mood; feelings of hopelessness or pessimism; feelings of guilt, worthlessness, or helplessness; loss of interest or pleasure in hobbies and activities that were once enjoyed; decreased energy, fatigue, or being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of major depressive disorder are described in, e.g., DSM-IV.

Anxiety is a cardinal symptom of many psychiatric disorders as well as a disease in itself Symptoms of anxiety commonly are associated with depression and especially with dysthymic disorder (chronic depression of moderate severity), panic disorder, agoraphobia and other specific phobias, obsessive-compulsive disorder, eating disorders and many personality disorders. Anxiety in humans includes those further divisions set out in the DSM-IV.

Use of Telomere Length and Telomerase Activity for Diagnosing Depression

As described herein in the Examples section, total lifetime days of depression are significantly and inversely correlated with telomere length. Thus, in one aspect, the present invention provides a method of diagnosing chronic depression in a subject by measuring telomere length in a sample from the subject (e.g., a sample from blood, lymph, saliva, cerebrospinal fluid, urine, tissue biopsy, or hair follicles) and determining whether the telomere length from the sample is shorter than a control value, wherein the control value is the telomere length of a non-depressed subject. Additionally, telomerase activity is higher in unmedicated depressed individuals as compared to matched healthy controls. Thus, in another aspect, the present invention provides a method of diagnosing depression in a subject by measuring telomerase activity in a sample from the subject and determining whether the telomerase activity from the sample is higher than a control value, wherein the control value is the telomerase activity of a non-depressed subject.

Diagnosis involves determining a telomere length and/or level of telomerase activity of the invention in a subject and then comparing the telomere length and/or telomerase activity level to a baseline or range that can be adjusted for variables such as age. For diagnosis, typically the baseline value is representative of a telomere length and/or telomerase activity of the invention in a healthy person not suffering from a mood disorder or under the effects of medication or other drugs. Variation of lengths of telomere and/or levels of telomerase activity from the baseline range indicates that the subject has a mood disorder. In the case of telomere length, lengths shorter than baseline range would be consistent with a diagnosis of depression. In the case of telomerase activity, levels higher than baseline range would be consistent with a diagnosis of depression. Additionally, the combination of short telomere length and high telomerase activity is consistent with a diagnosis of depression.

Use of Telomere Length and Telomerase Activity for Predicting Risk of Depression Information about a subject's telomere length and telomerase activity can be utilized to predict the likelihood of the subject developing depression in the future. The combination of a subject's telomere length and telomerase activity yields a cell aging protection score (CAPS) for the subject, for which a poor CAPS score is associated with an increased risk of developing depression in the future, even more than one year after the measurement of CAPS score.

Thus, in one aspect, the present invention provides a method of predicting that a subject is at risk of developing depression by measuring telomere length and telomerase activity in a sample from the subject (e.g., a sample from blood, lymph, saliva, cerebrospinal fluid, urine, tissue biopsy, or hair follicles) and determining whether the telomere length from the sample is shorter than a first control or baseline value and whether the telomerase activity from the sample is lower than a second control or baseline value. In another aspect, the present invention provides a method of predicting that a subject is at risk of developing depression by measuring telomere length and telomerase activity in a sample from the subject and determining whether the telomere length from the sample is shorter than a first control or baseline value and whether the telomerase activity from the sample is higher than a second control or baseline value.

For predicting the risk of developing depression, telomere length and level of telomerase activity are measured in a subject and then compared to the telomere length and telomerase activity level of a baseline or range that can be adjusted for variables such as age. Typically, the baseline value is representative of a telomere length and/or telomerase activity of the invention in a healthy person not suffering from a mood disorder or under the effects of medication or other drugs. Variation of lengths of telomere and levels of telomerase activity from the baseline value indicates that the subject is at risk of developing at least some aspects of a mood disorder. In some embodiments, the telomere length and/or telomerase activity may vary from the baseline value by at least about 10%, 20%, 30%, 40%, 50%, 60%, 70%, 80%, 90%, or more. In the case of telomere length, lengths shorter than baseline (e.g., at least about 10%, 20%, 30%, 40%, 50% or less than the baseline telomere length) would be consistent with a prediction of increased risk of developing depression. In the case of telomerase activity, levels lower than baseline (e.g., at least about 10%, 20%, 30%, 40%, or 50% lower than the baseline telomere length) or higher than baseline (e.g., at least about 10%, 20%, 30%, 40%, or 50% higher than the baseline telomere length) would be consistent with a prediction of increased risk of developing depression. Additionally, the combination of short telomere length and low telomerase activity is consistent with a prediction of increased risk of developing depression.

A CAPS score is determined by comparing telomere length and telomerase activity for a subject of interest in a group of subjects and controlling for age and gender variables. In some embodiments, a subject of interest is classified as having a "poor" CAPS score if the subject ranks in the bottom 25% of the group of subjects for telomere length and telomerase activity (i.e., the subject of interest has a shorter telomere length and telomerase activity than at least 75% of the other group members). In some embodiments, a subject is classified as having a "poor" CAPS score if the subject ranks in the bottom 25% of the group of subjects for telomere length and in the top 25% for telomerase activity (i.e., the subject of interest has a shorter telomere length and higher telomerase activity than at least 75% of the other group members).

The diagnostic and prognostic methods of the present invention rely on routine techniques in the fields of genetics and molecular biology. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994).

For nucleic acids, sizes are given in either kilobases (kb) or base pairs (bp). These are estimates derived from agarose or acrylamide gel electrophoresis, from sequenced nucleic acids, or from published DNA sequences. Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

In some embodiments, the telomere length and/or telomerase activity level and/or oxidative stress markers of the invention are measured by taking a blood, lymph, saliva, cerebrospinal fluid, urine, tissue biopsy, or hair follicle sample from a patient and measuring the length of a telomere and/or level of telomerase activity of the invention in the sample using any number of detection methods, such as those discussed herein.

The telomerase of the invention may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

Telomerase activity levels can be measured by a PCR-based detection method that measures the activity of the telomerase to elongate a nucleotide template. This method is generally known as TRAP (telomeric repeat amplification protocol). Methods for performing TRAP analysis are available commercially, e.g., TRAPEZE® RT Telomerase Detection Kit (Millipore). Briefly, this method utilizes polymerase chain reaction (PCR), as discussed below, to assess the activity of an extracted telomerase in adding telomeric repeats to the end of a substrate oligonucleotide. The reaction product may be visualized by radiolabeling or by non-radioactive staining of products by SYBR® Green or ethidium bromide. Optionally, fluorescence energy transfer primers which fluoresce only upon incorporation into TRAP products and can be used to generate fluorescently labeled TRAP products which permit quantitative analysis of telomerase activity.

Telomerase activity can be measured by immunoassay. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassay s can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)).

Analysis of telomere length can be achieved using routine techniques such as Southern analysis, reverse-transcriptase polymerase chain reaction (RT-PCR), or any other methods based on hybridization to a nucleic acid sequence that is complementary to a portion of the nucleotide sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid sequences can be performed using techniques known in the art including, without limitation, microarrays, polymerase chain reaction (PCR)-based analysis, sequence analysis, fluorescent in situ hybridization (FISH), comparative genomic hybridization (CGH), and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260: 1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SN-UPE) and pyrosequencing.

In some embodiments, telomere length is measured by a quantitative PCR (qPCR) method that quantifies the ratio of telomeric product compared to a single copy gene, as described in Cawthon, *Nuc. Acids Res.*, 30(10):e47 (2002). Briefly, genomic DNA is subjected to qPCR reactions for either a telomeric product or a single copy gene product, such as human beta-globin. A ratio of telomere repeat copy number to single copy gene copy number is then calculated, and relative ratios of telomere repeat copy number to single copy gene copy number can then be determined for control sample versus experimental sample in order to determine whether there is a relative length difference in telomeric DNA between the control sample and experimental sample. The qPCR method of measuring telomere length is further described herein in Example 1.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.*, 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

Use of Telomere Length and Telomerase Activity for Predicting a Subject's Suitability for Treatment and Efficacy of Treatment Depressed subjects having PBMC telomerase activity levels lower relative to other depressed subjects, and depressed subjects whose PBMC telomerase activity levels increase the most with anti-depressant treatment, show the greatest benefit from anti-depressant treatment. Accordingly, in one aspect the present invention provides a method of determining that a subject is a suitable candidate for an anti-depressant treatment to alleviate a mood disorder by measuring telomerase activity in a sample from the subject prior to administration of the anti-depressant treatment and determining whether the telomerase activity from the sample is lower than a control value, wherein telomerase activity in the sample from the subject that is lower than the control value indicates that the subject is likely to respond to the anti-depressant treatment. In some embodiments, the control value is a baseline telomerase activity cutoff value of 9.5 units/10,000 cells, and a suitable candidate for treatment has a baseline telomerase activity level of less than 9.5 units/10,000 cells. In some embodiments, the control value is a baseline telomerase activity cutoff value of 9.0 units/10,000 cells, and a suitable candidate for treatment has a baseline telomerase activity level of less than 9.0 units/10,000 cells.

Furthermore, depressed subjects having a ratio of telomere length to telomerase activity that is relatively higher than the telomere length-telomerase activity ratio in other depressed subjects are likely to have superior responses to anti-depressant treatment. As used herein, "relatively higher" means a ratio of telomere length to telomerase activity that is at least about 10% higher, at least 20% higher, at least 30% higher, at least 40% higher, at least 50% higher, at least 60% higher, at least 70% higher, at least 80% higher, at least 90% higher, or 100% higher or more than a control value. The control value may be the ratio of telomere length to telomerase activity in a control (e.g., non-depressed) subject or group of subjects, or alternatively the control value may be the ratio of telomere length to telomerase activity in a depressed subject or group of subjects. Accordingly, the present invention also provides a method of determining that a subject is a suitable candidate for anti-depressant treatment by measuring telomere length and telomerase activity in a sample from the subject prior to administration of the anti-depressant treatment and determining the ratio of telomere length to telomerase activity in the sample.

In another aspect, the present invention provides a method of assessing that an anti-depressant treatment to alleviate a mood disorder is efficacious by measuring telomerase activity in a first sample from the subject taken prior to administration of the anti-depressant treatment; measuring telomerase activity in a second sample from the subject taken during administration of the anti-depressant treatment; and determining that the telomerase activity in the second sample is higher than the telomerase activity in the first sample. In some embodiments, an anti-depressant treatment to alleviate a mood disorder is efficacious if the telomerase activity in the second sample is at least 10% higher, at least 20% higher, at least 30% higher, at least 40% higher, at least 50% higher, at least 60% higher, at least 70% higher, at least 80% higher, at least 90% higher, or 100% higher or more than the telomerase activity in the first sample.

Efficacy of treatment can alternatively be measured by determining a baseline telomerase activity level in a first sample from a subject, subsequently measuring a delta or changed telomerase activity level in a second sample from the subject, and comparing the delta telomerase activity level to the baseline telomerase activity level, wherein an increase in telomerase activity in the delta as compared to the baseline, or a decrease in telomerase activity that is no more than about 2.0-2.5 units/10,000 cells, indicates that the subject is responding to treatment. As used herein, "response" to anti-depressant treatment refers to an improvement in depressive symptoms in a subject (i.e., decrease in depression) of at least 10%, 20%, 30%, 40%, 50%, 60%, 70%, 80%, 90% or more as compared to the subject's depressive symptoms prior to treatment. Response to anti-depressant treatment can be measured, e.g., using a depression assessment scale such as the Hamilton Depression Rating Scale. In some embodiments, a baseline telomerase activity level in a subject of less than 9.5 units/10,000 cells and a delta telomerase activity level that is increased above baseline, that is the same as the baseline, or that is a decrease of no more than 2.0 units/10,000 cells indicates that the subject is responding to anti-depressant treatment. In some embodiments, a baseline telomerase activity level in a subject of less than 9.0 units/10,000 cells and a delta telomerase activity level that is increased above baseline, that is the same as the baseline, or that is a decrease of no more than 2.5 units/10,000 cells indicates remission of depression in the subject. As used herein, "remission" is an improvement in depressive symptoms (i.e., decrease in depression) to a level that corresponds to a Hamilton Depression Rating Scale score less than or equal to 7.

As described herein, a baseline telomerase activity level of less than 9.5 units/10,000 cells yields a sensitivity of 75%, a specificity of 75%, and a diagnostic accuracy of 75% for predicting response to anti-depressant treatment. A delta telomerase activity level that is increased above baseline or that is a decrease of no more than 2.0 units/10,000 cells yields a sensitivity of 78% and a specificity of 100% for predicting response to anti-depressant treatment. As described herein, a baseline telomerase activity level of less than 9.0 units/10,000 cells yields a sensitivity of 50%, a specificity of 88%, and a diagnostic accuracy of 69% for predicting remission of depression. A delta telomerase activity level that is increased above baseline or that is a decrease of no more than 2.5 units/10,000 cells yields a sensitivity of 56% and a specificity of 100% for predicting remission of depression. One of skill in the art will understand that the cutoff values for baseline and delta telomerase activity levels can be varied in order to adjust sensitivities and specificities.

As used herein, the term "providing a prognosis" refers to providing a prediction of suitability for treatment for depression and providing a prediction of the probable course and outcome of treatment for depression. In some embodiments, the prognosis will be made prior to the administration of an anti-depressant treatment. In some embodiments, the prognosis will be made after administration of an anti-depressant treatment, e.g. for indicating that a subject is not likely to respond to the anti-depressant treatment being administered or for determining that another anti-depressant treatment should be administered.

For predicting a subject's suitability for treatment or for predicting efficacy of treatment, the same methods of measuring telomere length and telomerase activity are used as described above.

Anti-depressant treatment may include any agent or any form of psychological treatment or psychotherapy typically used to treat clinical depression, or a combination of anti-depressant agents and psychotherapy. Anti-depressant agents include compounds of different classes including, for example, selective serotonin reuptake inhibitors (e.g., sertraline, escitalopram, citalopram, fluoxetine, fluvoxamine, or paroxetine), tricyclic antidepressants (e.g., desipramine), and dopamine reuptake inhibitors (e.g, bupropion). One of skill in the art will be able to determine a particular anti-depressant agent is suitable for a particular subject.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular anti-depressant medication in a particular patient.

It is understood that the examples and embodiments described herein are for illustrative purposes only and that various modifications or changes in lights thereof will be suggested to persons skilled in the art and are to be included within the spirit and purview of this application and scope of the appended claims.

IV. Examples

EXAMPLE 1

Telomere Shortening in Chronic Major Depression

This study explored the possibility that "accelerated aging" in depression occurs at the level of DNA and is manifest as telomere shortening in blood leukocytes. It was hypothesized that such changes are related to specific cytotoxic biochemical mediators, such as pro-inflammatory cytokines and oxidative stressors, which are often elevated in depression. It was predicted that depressed individuals would have shorter leukocyte telomeres than matched controls, that telomere length would be inversely correlated with lifetime exposure to depression, and that telomere length would be inversely correlated with oxidative stress and inflammatory markers.

Methods

Eighteen subjects with Major Depressive Disorder (MDD), diagnosed with the Structured Clinical Interview for DSM-IV-TR (SCID) (First M B, Spitzer R L, Gibbon M, *Structured Clinical Interview for DSM-IV-TR Axis I Disorders, Research Version, Patient Edition* (SCID-I/P). New York: New York State Psychiatric Institute, Biometrics Research (2002)), and 17 individually matched healthy controls (matched by gender, ethnicity and age ±3 years) were recruited and gave informed consent to participate in this study, which was approved by the University of California, San Francisco (UCSF) Committee on Human Research (CHR). Depressed subjects were all outpatients; they and the controls were recruited by fliers, bulletin board notices, Craigslist postings, newspaper ads and, in the case of depressed subjects, clinical referrals. Subjects we paid for their participation. SCID diagnostic interviews were conducted by an experienced clinical psychologist and were clinically verified by a separate psychiatric interview with a Board-certified psychiatrist. Depressed subjects with psychosis or bipolar histories were excluded, although co-morbid anxiety disorders were allowed when the depressive diagnosis was considered to be the primary diagnosis, with the exception of post-traumatic stress disorder, which was excluded, since it may have important differences in stress hormone regulation (Yehuda R, *Annals of the New York Academy of Sciences*, 1071:137-166 (2006)). Healthy controls were also screened with the SCID, and were required to have no present or past history of any DSM-IV Axis I or Axis II diagnosis. Potential subjects were also excluded if they met SCID criteria for alcohol or substance abuse within 6 months of entering the study. Subjects in both groups were medically healthy (assessed by physical examination, review of systems and screening laboratory tests), had no acute illnesses or infections, and had not had any vaccinations within 6 weeks of entering the study. All subjects (depressed and control) were free of any psychotropic medications, including antidepressants, antipsychotics and mood stabilizers, as well as any hormone supplements, steroid-containing birth control or other interfering medications (e.g. statins) or vitamin supplements above the U.S. Recommended Daily Allowances (e.g. Vitamin C, 90 mg/day), for a minimum of 6 weeks before entry into the study (with the exception of short-acting sedative-hypnotics, as needed, up to a maximum of 3 times per week, but none within one week prior to testing).

Procedure

Subjects were admitted as outpatients to the UCSF Clinical and Translational Science Institute's Clinical Research Center at 8:00 am, having fasted (except water) since 10:00 pm the night before. Before proceeding with testing, all subjects were required to test negative on a urine toxicology screen (measuring the presence of abused drugs) and, in women of child-bearing capacity, a urine pregnancy test. After the subjects sat quietly for 45 minutes, blood samples were obtained for leukocyte telomere length, oxidative stress markers (F2-isoprostanes and the anti-oxidant, Vitamin C) and IL-6 levels. Blood for the telomere length assay was collected into Cell Preparation Tubes (Becton-Dickinson Vacutainer CPT) containing a Ficoll separation gradient and stored frozen. DNA was prepared from whole blood using commercially available reagents (Gentra Puregene Blood Kit, Qiagen, Valencia, Calif.). Blood for the F2-isoprostane assay was collected into EDTA tubes with no vacuum, and blood for the Vitamin C assay was collected into foil wrapped serum separator tubes. Blood for IL-6 assay was collected into serum separator tubes. Total lifetime duration of depression was estimated in the depressed subjects using the life history methods of Sheline (Sheline Y I, *J Neurosci*, 19(12):5034-5043 (1999)) and Post (Post R M, Roy-Byrne P P, Uhde T W, *Am J Psychiatry*, 145(7):844-848 (1988)), supplemented with information derived from the SCID interview and the Antidepressant Treatment History Form (ATHF) (Sackeim H A, *J Clin Psychiatry*, 62(suppl 16):10-17 (2001)), which documents depressive episode durations as well as durations of antidepressant treatment, including the doses used and the treatment response. Lifetime depression history determinations and telomere assays were performed blind to each other.

Assays

For telomere length, the telomere length measurement assay was adapted from the published original method (Cawthon R M, *Nucleic Acids Res.,* 30(10):e47 (2002)). The rationale of this method is that the longer the telomeres are in each sample, the more PCR product will be generated in PCR reactions using primers specific for the telomeric DNA. PCR product can be quantified by quantitative PCR using a serially diluted standard DNA and the standard curve method. To normalize the quantity of the input DNA, a single copy gene is amplified in parallel as well. The ratio of the telomeric product (T) vs. the single copy gene (S) reflects the average length of the telomeres, wherein a first sample having a higher T/S ratio than a second sample indicates that the first sample has a longer telomere than the second sample.

Briefly, the T and S values of each sample were determined by quantitative PCR using the following primers: tel1b [5'-CGGTTT(GTTTGG)5GTT-3'], used at a final concentration of 100 nM, and tel2b [5'-GGCTTG(CCTTAC)5CCT-3'], used at a final concentration of 900 nM, for T; and hbg1 [5' GCTTCTGACACAACTGTGTTCACTAGC-3'], used at a final concentration of 300 nM, and hbg2 [5'-CACCAACTTCATCCACGTTCACC-3'], used at a final concentration of 700 nM, for S (human beta-globin). The final reaction mix contained 20 mM Tris-HCl, pH 8.4; 50 mM KCl; 200 µM each dNTP; 1% DMSO; 0.4× Syber Green I; 22 ng *E. coli* DNA per reaction; 0.4 Units of Platinum Taq DNA polymerase (Invitrogen) per 11 microliter reaction; and 0.5-20 ng of genomic DNA. Tubes containing 26, 8.75, 2.9, 0.97, 0.324, and 0.108 ng of a reference genomic DNA from HeLa cells were included in each PCR run to quantify the T and S values relative to the reference DNA sample by the standard curve method.

All PCRs were carried out on a Roche Lightcycler 480 real-time PCR machine with 384-tube capacity (Roche Diagnostics Corporation, Indianapolis, Ind.). The telomere thermal cycling profile consisted of: cycling for T (telomeric) PCR: denature at 96° C. for 1 second, anneal/extend at 54° C. for 60 seconds, with fluorescence data collection, 30 cycles; cycling for S (single copy gene) PCR: denature at 95° C. for 15 seconds, anneal at 58° C. for 1 second, extend at 72° C. for 20 seconds, 8 cycles; followed by denature at 96° C. for 1 second, anneal at 58° C. for 1 second, extend at 72° C. for 20 seconds, hold at 83° C. for 5 seconds with data collection, 35 cycles. To control for inter-assay variability, 8 control DNA samples were included in each run. For each of the 8 control samples, T/S ratio of each control DNA was divided by the average T/S for the same DNA from 10 runs to get a normalizing factor; the average normalizing factor for all 8 samples was used to correct the participant DNA samples to get the final T/S ratio. The T/S ratio was measured twice; when the duplicate T/S value and the initial value varied by more than 7%, the samples were assayed for a third time and the two closest values were reported. The inter-assay coefficient of variation (CV) for telomere length measurement was 2-4%.

To convert T/S ratio to base-pairs, the above method was used to determine the T/S ratios, relative to the same reference DNA, for a set of genomic DNA samples from the human fibroblast primary cell line IMR90 at different population double (PD) as well as with the telomerase protein subunit gene hTERT infected on a lentiviral construct. This set of the DNA samples represents different T/S ratios from the same parental cell line. The mean telomeric restriction fragment length from the DNA samples is determined using Southern blot analysis and the slope of the plot of mean TRF length versus T/S for these samples served as the conversion factor for calculation of approximate telomere lengths, in base-pairs (bp), for each T/S ratio in this study.

For oxidative stress, the most physiologically relevant assessment of net oxidative stress involves the joint assessment of oxidation by-product and anti-oxidants (Voss P, Siems W, *Free radical research,* 40(12):1339-1349 (2006); Cherubini A, *Free radical biology & medicine,* 39(7):841-852 (2005); Block G et al., *American journal of epidemiology,* 156(3):274-285 (2002)). In this study, overall oxidative stress was assessed as the ratio of one of the major oxidative by-products, F2-isoprostanes (Morrow J D et al., *Drug Metab Rev.,* 31(1):117-139 (1999); Morrow J D, Roberts L J, *Methods Mol Biol.,* 186:57-66 (2002); Mariani E et al., *J Chromatogr B Analyt Technol Biomed Life Sci.,* 827(1):65-75 (2005)), with one of the major circulating anti-oxidant compounds, ascorbic acid (Vitamin C) (Block G et al., *American journal of epidemiology,* 156(3):274-285 (2002); Dietrich M et al., *Nutrition and cancer,* 45(2):176-184 (2003)). F2-isoprostanes (a collection of isomers) were measured by a gas chromatography-mass spectrometry (GC-MS)-based method as described by Morrow (Morrow J D, Roberts L J et al., *Methods Enzymol.,* 300:3-12 (1999)) and Gross (Gross M et al., *Clin Chem.,* 51(1):125-131 (2005)). The isoprostanes were extracted from the participant's sample, and deuterated 8-iso-prostaglandin F2 alpha was added as an internal control. Unlabeled purified F2-isoprostane was used as a calibration standard for the assay. Vitamin C was assayed by Kronos Institute Laboratories, Phoenix, Ariz., using an Agilent 1100 Series Liquid Chromatograph with UV spectrophotometric detection (Margolis S A, Schapira R M et al., *Journal of Chromatography B.,* 690:25-22 (1997)). The serum sample was preserved by adding an equal volume of metaphosphoric acid. Samples were analyzed using external standards with UV spectrophotometric detection at 243 nm wavelength. Method detection limits are 10 n/ml. Recoveries were consistently in excess of 90%, and CV ranged from 4% to 15%.

For IL-6 quantification, samples were collected in 10 ml SST tubes (Becton Dickinson, Franklin Lakes, N.J.). Serum was frozen and stored at −80° C. A high sensitivity enzyme-linked immunosorbent assay was used to quantify IL-6 concentrations (R&D Systems, Minneapolis, Minn.). The assay sensitivity was <0.1 pg/ml, and average intra- and inter-assay CVs were 7% and 8% respectively. Each sample was analyzed in duplicate according to manufacturer protocol.

Statistics

The impact of age, gender, body-mass index (BMI), and lifetime and current tobacco use as potential confounds was assessed first; significant effects of age and gender on telomere length were found, and significant effects of age and BMI on IL-6 were found. Lifetime and current tobacco use were not significantly related to any of these variables. Consequently, all analyses were controlled for age and gender, and analyses involving IL-6 were additionally controlled for BMI. Before analyzing the data, distributions were examined for normality; non-normal distributions were natural log transformed (Ln) when necessary.

Between-group comparison of the demographic variables was by independent sample t-tests, Chi square tests and independent sample Kruskal-Wallis tests. Other between-group data, when covariates were applied, were analyzed by analysis of covariance (ANCOVA). Correlations between variables were assessed by hierarchical linear regression, with age and sex (and BMI, in the case of IL-6) entered first. All tests were 2-tailed with an alpha=0.05.

Results

Demographics. The mean age of the depressed and control subjects did not significantly differ (36.6±11.8 [SD] vs. 36.8±11.0 years [range 25-69 years], respectively), nor did the gender distribution (65% female in each group), ethnicity distribution or body-mass index (24.8±3.7 vs. 26.2±5.7, respectively). The subject groups also did not significantly differ in current and past alcohol and nicotine consumption, in marital status, in highest educational level attained, or in self-rated socioeconomic status (Adler N et al., Health Psychol., 19:586-592 (2000)), although mean household income was significantly higher in the controls than in the depressed subjects (p<0.01). The mean 17-item Hamilton Depression Rating Scale (HDRS) (Hamilton M, Br J Soc Clin Psychol., 6(4):278-296 (1967)) rating in the depressed subjects was 19.3±3.9 (range 17-26), and the mean chronicity of depression (i.e., lifetime months of depression) was 156.5±134.8 months (range 9.3-418.9 months), corresponding to a mean ratio of lifetime depression to chronological age of 0.36±0.27 (range 0.02-0.88) (This ratio has a theoretical minimum of zero, corresponding to no lifetime depression, to a maximum of one, corresponding to a complete lifetime of depression.) Demographic characteristics of the subjects are provided in Table 1.

TABLE 1

Characteristics of Depressed and Control Subjects

| | Controls | Depressed | p |
|---|---|---|---|
| Age (Years) | 36.6 ± 11.8 | 36.8 ± 11.0 | ns |
| Gender (% Female) | 65 | 65 | ns |
| Ethnicity (% Caucasian, African-American, Asian, Other or Mixed) | 75, 15, 5, 5 | 68, 11, 11, 11 | ns |
| Body-Mass Index | 24.8 ± 3.7 | 26.3 ± 5.9 | ns |
| No Tobacco Ever (%) | 56 | 69 | ns |
| Current Tobacco Use (% None, Sometimes, Daily) | 83, 11, 6 | 83, 17, 0 | ns |
| Subjective Socio-economic Status[1] | 6.45 ± 1.13 | 5.75 ± 1.60 | ns |
| Years of Education | 15.82 ± 2.28 | 15.28 ± 2.06 | ns |
| Household Income ($) | 68,000 ± 8,475 | 24,500 ± 12,000 | <0.01 |

[1]Subjective socioeconomic status was measured using a 10-rung ladder version of the MacArthur Scale of Subjective Social Status (Adler N et al., Health Psychol., 19: 586-592 (2000)).

Telomere length. Leukocyte telomere length (in bp) was marginally shorter in depressed subjects than in controls (mean±SD: depressed: 5101±425 bp, vs. controls: 5141±282 bp; difference=40 bp), but this was not statistically significant (F=0.17, controlling for age and gender). This average difference is roughly equal to one year of accelerated aging at the level of the leukocyte, assuming an average yearly attrition of 31-66 by (Epel E S et al., Proceedings of the National Academy of Sciences of the United States of America, 101(49):17312-17315 (2004)). However, not all depressed subjects are equally likely to show shortened telomeres, since the lifetime exposure to depression varied greatly between subjects (e.g., from a minimum of 9.3 months to a maximum of 418.9 months in this sample), and since telomere length is believed to reflect cumulative lifetime history of cellular reproduction and of exposure to cytotoxic stimuli such as oxidation and inflammation (von Zglinicki T, Trends Biochem Sci., 27(7):339-344 (2002); Aviv A, Sci Aging Knowledge Environ., 2004 (51):pe43 (2004); Epel E S, Hormones (Athens), 8(1):7-22 (2009); von Zglinicki T, Martin-Ruiz C M, Current molecular medicine, 5(2):197-203 (2005)) and to stress (Epel E S, Hormones (Athens), 8(1):7-22 (2009); Epel E S et al., Proceedings of the National Academy of Sciences of the United States of America, 101(49):17312-17315 (2004)). Therefore, telomere length was examined in the depressed group as a function of cumulative (lifetime) duration of depression, corrected for age and gender.

Next, lifetime exposure to depression was utilized as a categorical independent variable, comparing the control subjects to the depressed subjects in the highest tertile and in the highest half of lifetime depression duration. Telomere length within the depressed subjects was significantly inversely correlated with lifetime depression duration (controlling for age and gender); individuals with greater lifetime duration of major depression had significantly shorter telomeres (F=4.70, p<0.05) (FIG. 1). This relationship remained statistically significant when lifetime and current tobacco use and BMI were additionally controlled. When depressed individuals in the upper tertile of lifetime exposure to depression (>20 years cumulative duration) were compared to controls, highly significant differences in telomere length were observed (controls: 5141±282 bp vs. depressed: 4792±258 bp; F=8.28, p=0.005, controlling for age and gender). This difference also remained significant when lifetime and current tobacco use and BMI were controlled. This difference in mean telomere length (349 bp) is equivalent to approximately 9 years of "accelerated aging" at the level of the leukocyte. The fact that this difference is highly significant after controlling for age suggests that greater lifetime duration of depression was not simply a proxy for older age, which is also associated with shorter telomeres. With a more liberal cutoff for lifetime exposure to depression (above the median, 9.2 years cumulative duration), the difference in leukocyte telomere length between groups remained significant (controls: 5141±282 bp vs. depressed: 4860±349 bp; difference=281 bp; F=2.87, p=0.05, controlling for age and gender).

In an exploratory secondary analysis, the impact of lifetime antidepressant treatment on this relationship was examined. Lifetime exposure to untreated depression remained significantly inversely correlated with telomere length (F=3.62, p<0.05) but lifetime exposure to depression, while receiving antidepressants, was not (F=2.50, p=0.11), although the lengths of time subjects had been actively depressed while receiving antidepressant medication spanned a relatively short range (range: 0.0 to 31.2 months).

Figure 2:
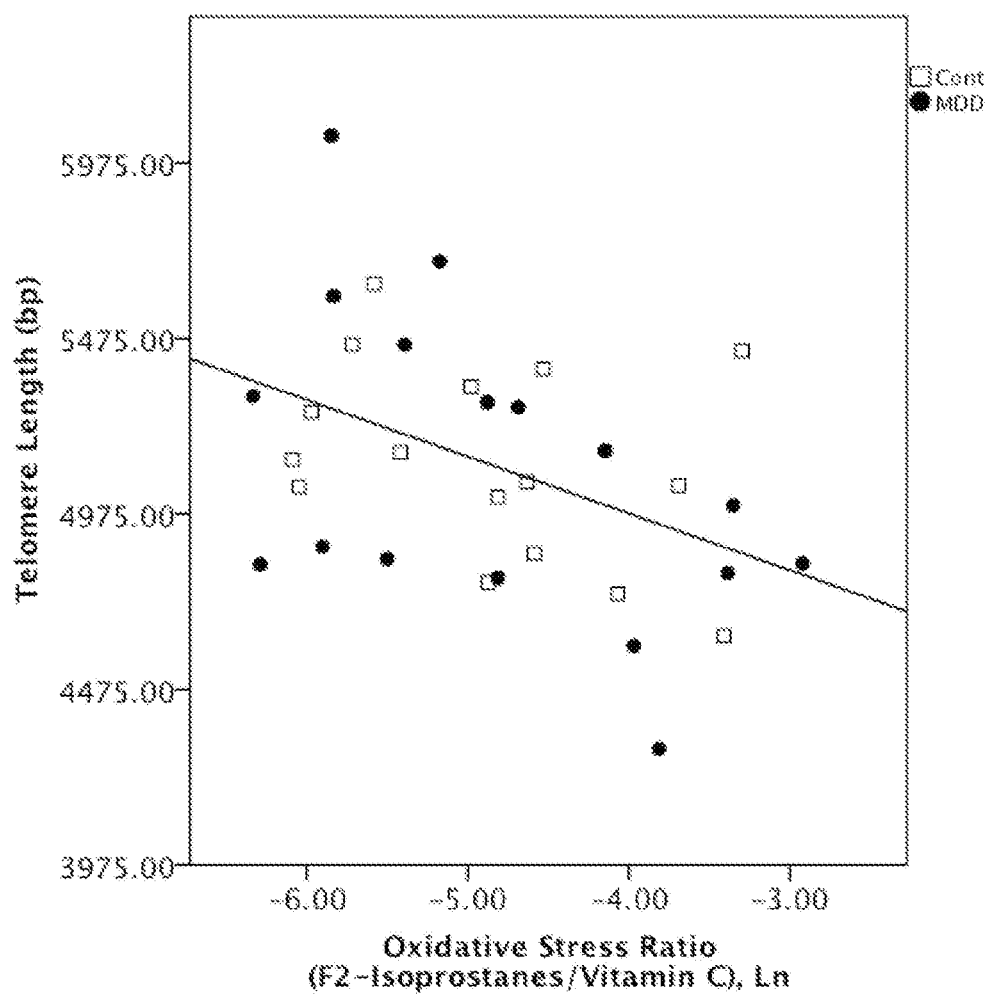
FIG. 2. Relationship between oxidative stress ratio (F-2 isoprostanes/Vitamin C ratio, Ln transformed) and leukocyte telomere length (in base pairs, bp). Filled circles represent depressed subjects ("MDD") ($F=6.04$, $p<0.01$, controlling for age and sex), and open squares represent controls ("Cont") ($F=4.38$, $p<0.05$, controlling for age and sex). In the combined sample (depressed plus controls), the relationship was also statistically significant ($F=8.21$, $p=0.000$, controlling for age and sex).
Figure 3:
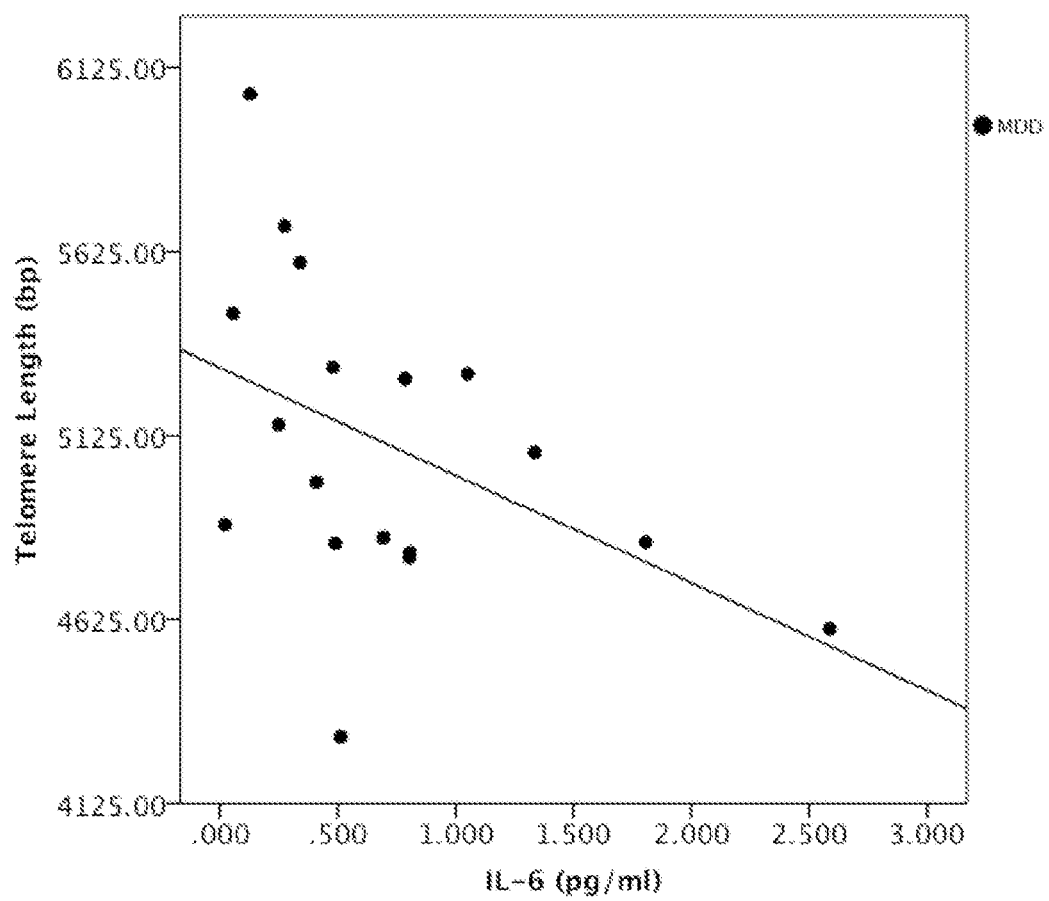
FIG. 3. Relationship between serum IL-6 concentrations (pg/ml) and leukocyte telomere length (in base pairs, bp). The data represent depressed subjects ("MDD") ($F=3.29$, $p<0.05$, controlling for age, sex and BMI). The relationship missed significant in the combined sample (depressed plus controls) ($F=2.45$, $p=0.07$, controlling for age, sex and BMI) and was not significant in the controls alone ($F=2.28$, $p=0.13$, controlling for age, sex and BMI) (not shown).

Relationships between inflammation and oxidation markers and telomere length. In the combined sample (depressed plus control subjects), the oxidative stress ratio (F2-isoprostanes/vitamin C) was inversely correlated with telomere length (F=8.21, p=0.000, controlling for age and gender) (FIG. 2). This relationship remained significant in the separate depressed (F=6.04, p<0.01) and control groups (F=4.38, p<0.05). Considering the components of this ratio separately, vitamin C concentrations were significantly positively correlated with telomere length in the combined sample (F=4.72, p<0.01) as well as in the individual depressed (F=5.85, p<0.01) and control samples (F=4.04, p<0.05) (all controlled for age and gender). F2-isoprostane concentrations were significantly negatively correlated with telomere length in the combined sample (F=4.78, p<0.01, controlling for age and gender), but this relationship missed statistical significance in the separate depressed (F=2.59, p<0.10) and control groups (F=2.31, p=0.13). IL-6 concentrations were significantly inversely correlated with telomere length in the depressed group (F=3.29, p<0.05, controlling for age, gender and BMI) (FIG. 3), but not in the control group (F=2.28, p=0.13). In the combined sample, this relationship approached significance (F=2.45, p=0.07, controlling for age, gender and BMI).

Figure 10:
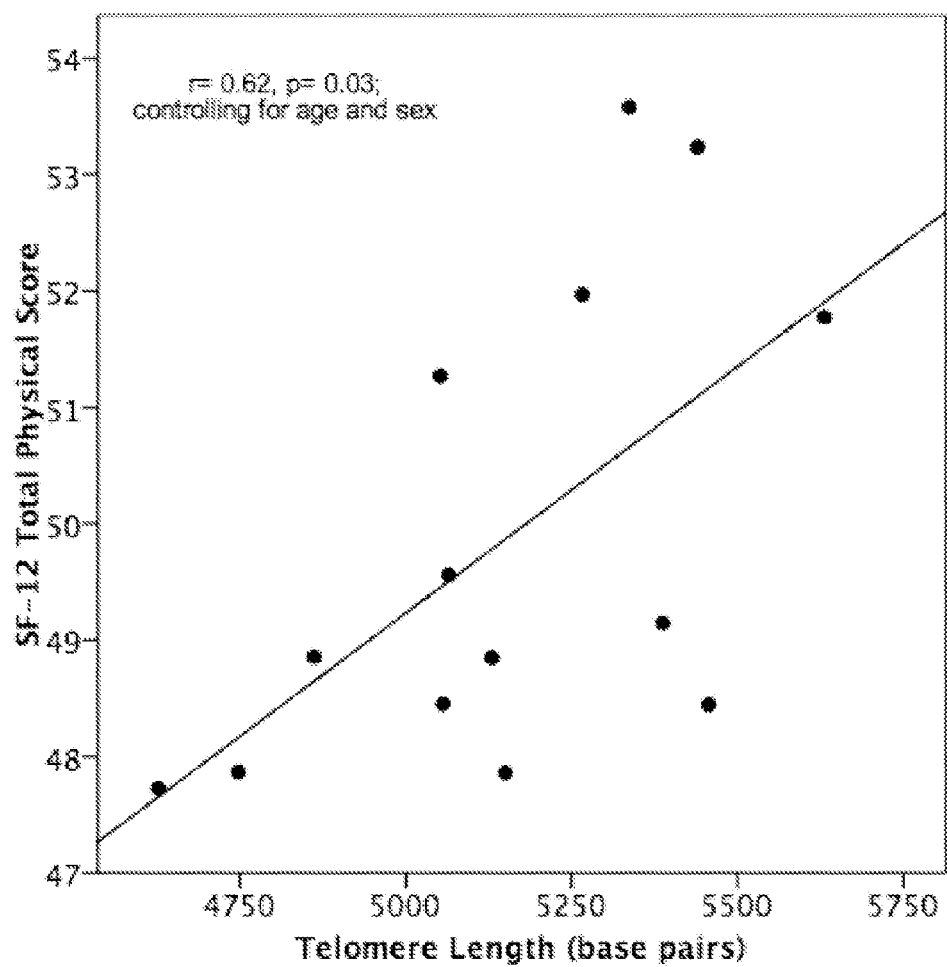
FIG. 10. Telomere length and perceived physical health. Fourteen healthy controls had leukocyte telomere length assessed and completed the self-rated SF-12 Health Inventory. In the Physical Health sub-scale of this inventory, higher numbers (ranging from 0 to 100) indicate better physical health. Longer telomere length, corrected for age and sex, was significantly correlated with better self-rated physical health ($r=0.62$, $p=0.03$).

Relationship between telomere length and perceived physical health. Fourteen healthy controls had leukocyte telomere length assessed and completed the self-rated SF-12 Health Inventory. In the Physical Health sub-scale of this inventory, higher numbers (ranging from 0 to 100) indicate better physical health. Longer telomere length, corrected for age and sex, was significantly correlated with better self-rated physical health (r=0.62, p=0.03) (FIG. 10). This finding is significant because self-reported health is a significant predictor of mortality. Therefore, telomere monitoring may be useful as a measure of health.

Discussion

As a group, depressed individuals, across a broad range of depressive chronicity, did not differ from controls in leukocyte telomere lengths. However, individuals with extensive life courses of major depression had significantly shorter leukocyte telomeres than age-, gender- and ethnicity-matched healthy controls. Importantly, the relationship between telomere length and lifetime duration of depression was significant after age was controlled, indicating that longer exposure to depression was not simply a proxy for more advanced age, which is also associated with telomere shortening. Since telomere length has been proposed as a biomarker of cell aging and a predictor of health and longevity (Aviv A, *Sci Aging Knowledge Environ.*, 2004 (51):pe43 (2004); Aviv A, *The journals of gerontology*, 61(8):871-873 (2006); Brouilette S et al., *Arteriosclerosis, thrombosis, and vascular biology*, 23(5):842-846 (2003); Epel E S et al., *Psychoneuroendocrinology*, 31(3):277-287 (2006); Epel E S et al., *Aging*, 1(1):81-88 (2009)), this finding may explain some of the excess medical morbidity and premature mortality seen in chronically depressed populations (Brown E S, Varghese F P, McEwen B S, *Biol Psychiatry*, 55(1):1-9 (2004); Musselman D L, Evans D L, Nemeroff C B, *Archives of general psychiatry*, 55(7):580-592 (1998); McCusker J et al., *Gen Hosp Psychiatry*, 29(4): 340-348 (2007); Irwin M R, Miller A H, *Brain, behavior, and immunity*, 21(4):374-383 (2007); Godbout J P, Johnson R W, *Neurologic clinics*, 24(3):521-538 (2006); Arfken C L, Lichtenberg P A, Tancer M E, *The journals of gerontology*, 54(3):M152-156 (1999); Schulz R et al., *Archives of internal medicine*, 160(12):1761-1768 (2000); Evans D L et al., *Biological psychiatry*, 58(3):175-189 (2005); Gump B B et al., *Stroke; a journal of cerebral circulation*, 36(1):98-102 (2005); Rapp M A et al., *Am J Geriatr Psychiatry*, 16(10): 844-852 (2008); Heuser I, *Maturitas*, 41 Suppl 1:S19-23 (2002)). Depressed individuals with less chronic courses, however, showed no significant differences in telomere length, compared to controls. This argues against short telomeres representing a pre-existing risk factor for major depression. Rather, it suggests that telomere shortening may progress with longer exposure to depression. Additionally, the findings of significant inverse correlations between telomere length and oxidative and inflammatory stress in the depressed subjects raise the possibility that these biochemical stressors contribute to telomere shortening in chronic depression. Oxidative stress was inversely correlated with telomere length in the depressed subjects and the controls, consistent with a general shortening effect of oxidation on telomeres (Houben J M et al., *Free radical biology & medicine*, 44(3):235-246 (2008); von Zglinicki T, *Trends Biochem Sci.*, 27(7):339-344 (2002); Aviv A, *Sci Aging Knowledge Environ.*, 2004(51):pe43 (2004); Wolkowitz O M et al., *Depression and Anxiety*, in press; Demissie S et al., *Aging cell*, 5(4):325-330 (2006)). IL-6 concentrations, however, were significantly correlated with telomere length in the depressed subjects but not in the controls. The reasons for this difference are unknown, although differences in specific patterns of inflammatory and anti-inflammatory cytokines may be important.

The degree of telomere shortening observed in the most chronically depressed individuals (those in the upper tertile of chronicity) corresponds to approximately nine years of "accelerated cell aging." This degree of "acceleration" accords well with that described in stressed maternal caregivers (9-17 years) (Epel E S et al., *Proceedings of the National Academy of Sciences of the United States of America*, 101(49):17312-17315 (2004)), in stressed spousal and offspring caregivers (4-8 years) (Damjanovic A K et al., *J Immunol.*, 179(6):4249-4254 (2007)) and in affectively ill individuals (over 10 years) (Simon N M et al., *Biological psychiatry*, 60(5):432-435 (2006)). In the caregiver study by Epel et al. (Epel E S et al., *Proceedings of the National Academy of Sciences of the United States of America*, 101(49):17312-17315 (2004)), telomere shortening was similarly found to be a function of the chronicity of caregiver stress. The study of affectively ill subjects by Simon et al. (Simon N M et al., *Biological psychiatry*, 60(5):432-435 (2006)) found a significant shortening of telomere length in the whole affectively ill sample rather than in just a more chronic subgroup, as here. However, it is important to note that the average lifetime duration of affective illness in their sample was 31.8±11.2 (SD) years, which is near the upper end of chronicity in the sample studied here (34.9 years). Accordingly, the estimate of accelerated aging from this study is in line with data from that prior study. Cumulatively, the results suggest that telomere shortening occurs as a function of lifetime duration of illness.

Shortened telomere length in chronic depression is consistent with findings in other chronically stressed and depressed populations (Damjanovic A K et al., *J Immunol.*, 179(6):4249-4254 (2007); Epel E S et al., *Proceedings of the National Academy of Sciences of the United States of America*, 101(49):17312-17315 (2004); Huzen J et al., *Age and ageing*, 39(2):223-227 (2010)), although it is not specific to stress or depression. Shortened telomeres have also been documented in a variety of pathologies associated with aging (Effros R B, *The journals of gerontology*, 64(5):511-515 (2009)). Interestingly, several medical and other conditions that are associated with shortened telomeres are also overly represented in major depression, e.g., cardiovascular disease (Brouilette S et al., *Arteriosclerosis, thrombosis, and vascular biology*, 23(5):842-846 (2003); Cawthon R M et al., *Lancet*, 361(9355):393-395 (2003); Brouilette S W et al., *Lancet*, 369(9556):107-114 (2007); Huzen J et al., *Front Biosci*, 15:35-45 (2010); Fitzpatrick A L et al., *American journal of epidemiology*, 165(1):14-21 (2007); Serrano A L, Andres V, *Circ Res.*, 94(5):575-584 (2004); Fuster J J, Andres V, *Circ Res.*, 99(11):1167-1180 (2006)), stroke (Fitzpatrick A L et al., *American journal of epidemiology*, 165 (1):14-21 (2007)), dementia and pre-dementia (Martin-Ruiz C et al., *Annals of neurology*, 60(2):174-180 (2006); Honig L S et al., *Annals of neurology*, 60(2):181-187 (2006); von Zglinicki T et al., *Laboratory investigation; a journal of technical methods and pathology*, 80(11):1739-1747 (2000); Grodstein F et al., *PLoS one*, 3(2):e1590 (2008)), decreased hippocampal volume (Grodstein F et al., *PLoS one*, 3(2): e1590 (2008)), diabetes (Adaikalakoteswari A, Balasubramanyam M, Mohan V, *Diabet Med.,* 22(9):1151-1156 (2005); Sampson M J et al., *Diabetes care,* 29(2):283-289 (2006)), osteoporosis (Valdes A M et al., *Osteoporos Int,* 18(9):1203-1210 (2007); Tamayo M et al., *Mutation research,* 683(1-2):68-73 (2010)) (although see (Sanders J L et al., *J Bone Miner Res.,* 24(9):1531-1536 (2009)), history of childhood maltreatment (Tyrka A R et al., *Biological psychiatry,* 66(7):681-685 (2009)) and dispositional pessimism (O'Donovan A et al., *Brain, behavior, and immunity,* 23(4):446-449 (2009)). Non-affective psychoses, including schizophrenia, are also associated with shortened leukocyte telomeres (Fernandez-Egea E et al., *Schizophrenia bulletin,* 35(2):437-442 (2009); Kao H T et al., *Mol Psychiatry,* 13(2):118-119 (2008); Yu W Y et al., *J Psychiatry Neurosci.,* 33(3):244-247 (2008)).

These findings suggest plausible biochemical mechanisms by which depression might result in shortened telomeres. Significant increases in oxidative stress (Irie M, Miyata M, Kasai H, *Journal of psychiatric research,* 39(6): 553-560 (2005); Forlenza M J, Miller G E, *Psychosomatic medicine,* 68(1):1-7 (2006); Ng F et al., *The international journal of neuropsychopharmacology/official scientific journal of the Collegium Internationale Neuropsychopharmacologicum (CINP),* 11(6):851-876 (2008); Tsuboi H et al., *Journal of psychosomatic research,* 56(1):53-58 (2004); Sarandol A et al., *Human psychopharmacology,* 22(2):67-73 (2007)) and inflammatory stress (Kiecolt-Glaser J K, Glaser R, *Journal of psychosomatic research,* 53(4):873-876 (2002); Licinio J, Wong M L, *Mol Psychiatry,* 4(4):317-327 (1999); Dhabhar F S et al., *Journal of psychiatric research,* 43(11):962-969 (2009); Miller A H, Maletic V, Raison C L, *Biological psychiatry,* 65(9):732-741 (2009); Dinan T G, *Current opinion in psychiatry,* 22(1):32-36 (2009); Howren M B, Lamkin D M, Suls J, *Psychosomatic medicine,* 71(2): 171-186 (2009)) have been described in major depression, although the reasons for these abnormalities are unclear. To the extent oxidative and inflammatory stress are chronically increased in depressed individuals, or to the extent depressed individuals have a compromised ability to prevent or recover from oxidative or inflammatory damage, these stressors could contribute to telomere shortening (Haendeler J et al., *Circ Res.,* 94(6):768-775 (2004); Tsirpanlis G et al., *Nephrology (Carlton),* 11(6):506-509 (2006); Sebastian C et al., *J Immunol.,* 183(4):2356-2364 (2009). Conversely, leukocyte telomere shortening, resulting in immunosenescence and impaired leukocyte function, can lead to increased inflammatory cytokine output (Effros R B, *The journals of gerontology,* 64(5):511-515 (2009)) and to increased oxidative stress (Sebastian C et al., *J Immunol.,* 183(4):2356-2364 (2009)), thus forming a vicious cycle (Kiecolt-Glaser J K, Glaser R, *Journal of psychosomatic research,* 53(4):873-876 (2002)). The significant correlations observed between oxidative and inflammatory stress and telomere length have not been previously reported in depressed subjects, but they are consistent with relationships between oxidative and inflammatory stress and telomere length in other populations. It is possible that leukocyte telomere shortening occurs across conditions that are characterized by chronic exposure to cytotoxic processes such as oxidation and/or inflammation or by increased leukocyte turnover (Bauer M E, Jeckel C M, Luz C, *Annals of the New York Academy of Sciences,* 1153:139-152 (2009)). For example, the study of chronically stressed maternal caregivers described above found that telomere length was inversely correlated with oxidative stress (the F2-isoprostane/Vitamin E ratio) (Epel E S et al., *Proceedings of the National Academy of Sciences of the United States of America,* 101(49):17312-17315 (2004)). Also, telomere shortening was significantly correlated with measures of oxidative stress in men with Type II diabetes (Sampson M J et al., *Diabetes care,* 29(2):283-289 (2006)). Telomere length has also been correlated with inflammatory markers. In community-dwelling older individuals, telomere shortening was associated with increased C-reactive protein (CRP) and IL-6 concentrations in men (but not in women) (Sanders J L et al., *J Bone Miner Res.,* 24(9):1531-1536 (2009)). In another study, caregivers of Alzheimer's Disease patients had shortened leukocyte telomeres along with increased in vitro-stimulated production of tumor necrosis factor (TNF)-alpha and IL-10 (Damjanovic A K et al., *J Immunol.,* 179(6):4249-4254 (2007)). A study of Alzheimer's Disease patients found that telomere length was inversely correlated with serum levels of TNF-alpha (Panossian L A et al., *Neurobiology of aging,* 24(1):77-84 (2003)). Even in healthy post-menopausal women, the psychological trait "dispositional pessimism" was associated both with shortened telomeres and with elevated IL-6 concentrations (O'Donovan A et al., *Brain, behavior, and immunity,* 23(4): 446-449 (2009)). Finally, in older individuals in the Cardiovascular Health Study, shortened telomeres were significantly correlated with increased IL-6 and CRP concentrations (Fitzpatrick A L et al., *American journal of epidemiology,* 165(1):14-21 (2007)).

In summary, this example shows that individuals with extensive life histories of major depression, even when corrected for age, have shortened leukocyte telomere length, and that this is correlated with measures of oxidative and inflammatory stress. Decreased telomere length in chronic depression is concerning, since similar magnitudes of telomere shortening have been related to increased risk of cardiovascular and other diseases and to premature mortality in various non-depressed populations. Telomere length measurements might help stage the degree or progression of medical risk in depressed individuals and thereby identify those in need of closer medical follow-up (Grodstein F et al., *PloS one,* 3(2):e1590 (2008)). Further, treatments aimed at maintaining telomere length (or treatments with anti-oxidative and anti-inflammatory effects) could become important treatment tools.

EXAMPLE 2

Leukocyte Telomerase Activity in Major Depression

This study characterized PBMC telomerase activity in unmedicated individuals with major depression compared to matched healthy controls, to determine whether pre-treatment levels of PBMC telomerase activity predict antidepressant response and whether antidepressant-induced changes in PBMC telomerase activity are related to treatment response.

Methods

Twenty subjects with Major Depressive Disorder (MDD), diagnosed with the SCID, and 18 matched healthy controls (matched by gender, ethnicity and age ±3 years) were recruited and gave informed consent to participate in this study. The study protocol and consent form were approved by the University of California, San Francisco (UCSF) Committee on Human Research. Depressed subjects were all outpatients; they and the controls were recruited by fliers, bulletin board notices, Craigslist postings, newspaper ads and, in the case of depressed subjects, clinical referrals. Subjects were paid for their participation, and depressed subjects received free antidepressant treatment during the treatment phase of the study as described below. SCID diagnostic interviews were conducted by an experienced clinical psychologist and were clinically verified by psychiatric interview with a Board-certified psychiatrist. Depressed subjects with psychosis or bipolar histories were excluded, although co-morbid anxiety disorders were allowed when the depressive diagnosis was considered to be the primary diagnosis, with the exception of post-traumatic stress disorder, which was excluded. Healthy controls were also screened with the SCID, and were required to have no present or past history of any DSM-IV Axis I or Axis II diagnosis. Potential subjects were also excluded if they met SCID criteria for alcohol or substance abuse within 6 months of entering the study. Subjects in both groups were medically healthy (as assessed by physical examination, review of systems and screening laboratory tests), had no acute illnesses or infections, and had not had any vaccinations within 6 weeks of entering the study. All subjects (depressed and control) were free of any psychotropic medications, including antidepressants, antipsychotics and mood stabilizers, as well as any hormone supplements, steroid-containing birth control or other interfering medications (e.g. statins) or vitamin supplements above the U.S. Recommended Daily Allowances (e.g. vitamin C, 90 mg/day), for a minimum of 6 weeks before entry into the study (with the exception of short-acting sedative-hypnotics, as needed, up to a maximum of 3 times per week, but none within one week prior to testing).

Procedure

Subjects were admitted as outpatients to the UCSF Clinical and Translational Science Institute (CTSI)'s Clinical Research Center at 8:00 am, having fasted (except water) since 10:00 pm the night before. Before proceeding with testing, all subjects were required to test negative on a urine toxicology screen (measuring the presence of abused drugs) and, in women of child-bearing capacity, a urine pregnancy test. After the subjects sat quietly for 45 minutes, blood samples were obtained for PBMC telomerase activity. Following blood collection, depressed subjects were rated with the 17-item version of the observer-rated Hamilton Depression Rating Scale (HDRS) (Hamilton M., *Br J Soc Clin Psychol*, 6(4):278-296 (1967)), and the depressed subjects and controls completed the self-rated Inventory of Depressive Symptomatology (IDS) (Rush A J et al., *Psychiatry research*, 18(1):65-87 (1986)) and the self-rated Perceived Stress Scale (PSS) (Cohen S et al., *Journal of Health and Social behavior*, 24:385-396 (1983)).

Following this baseline assessment day, 16 depressed subjects were prescribed a serotonin specific reuptake inhibitor antidepressant, sertraline, for eight weeks on an outpatient basis. One of the original group of 20 depressed subjects withdrew consent for treatment, two were dropped by the investigators because of the development of exclusion criteria (acute medical illnesses) and one dropped out by mutual agreement of the subject and the investigators due to depressive worsening during sertraline treatment, leaving 16 subjects completing eight weeks of antidepressant treatment. Sertraline was prescribed in an open-label manner, beginning with 50 mg per day, increasing to a maximum of 200 mg per day, as tolerated and as warranted by clinical response. In two cases, the beginning dose was initially lowered to 25 mg per day due to initial transient side effects. Medication compliance was monitored by pill counts and by plasma antidepressant levels as described below at Week 4 and Week 8 of treatment. Following eight weeks of sertraline treatment, depressed subjects were re-admitted as outpatients to the UCSF CTSI at 8:00 am and followed a procedure identical to that used on the baseline (pre-treatment) day. Blood was obtained for PBMC telomerase assay and plasma antidepressant levels, and the HDRS was repeated. One subject failed to have telomerase activity assayed at Week 8, leaving 15 depressed subjects with Week 8 telomerase data.

Assays

Telomerase activity was measured using a telomere repeat amplification protocol (TRAP). For the TRAP assay, 10 mL of peripheral blood was collected and anticoagulated in Vacutainer® (Becton-Dickinson) CPT tubes with density gradient polymer gel and sodium citrate additives. The peripheral blood mononuclear cell (PBMC) fraction was isolated from each blood sample using density gradient centrifugation according to the instructions for the CPT tubes. Immediately following centrifugation, the PBMC layer was collected. Cells were washed three times in phosphate-buffered saline (PBS) and were resuspended in PBS. Live cells were counted with Trypan blue staining solution with a hemocytometer. Extracts corresponding to 5000 cells/4 were made based on the protocol provided in the commercially available TRAPeze® telomerase detection kit (Chemicon, Temecula, Calif.). The extracts were stored at −80° C. until use.

Quantification of telomerase activity was measured from the extract using the telomeric repeat amplification protocol (TRAP) as previously described (Kim and Wu, 1997) with the TRAPeze® kit. Between 2,000 to 10,000 cells were used for TRAP reactions to ensure that the assay was in the linear range for each sample. The reaction was carried out according to manufacturer's instructions, using the PCR program: 94° C. for 2 min; 94° C. for 30 sec; 59° C. for 30 sec; for 30 cycles. The products were fractionated on a 10% polyacrylamide 8M urea sequencing gel, exposed to a phosphorimager plate overnight, and scanned on a STORM 860 molecular imager (GE Healthcare, Piscataway, N.J.). The 293T cancer cell line was used as a positive telomerase activity control and reference standard. Telomerase activity was quantified using ImageQuant 5.2 software (GE Healthcare, Piscataway, N.J.). Signals from the product ladders on the gels were added and normalized against the signal from internal control band for the same lane to yield a product/internal control value. For each telomerase activity assay reaction, the product/internal value was divided by the product/internal control value from twenty 293T cells and then multiplied by 20 to get the final telomerase activity, defined as 1 unit=the amount of product from one 293T cell/10,000 PBMCs. Resting PBMCs had telomerase activities in the range of 1-30 units. The inter-assay variability (CV) was 6.7%.

Statistics

The impact of age, gender, BMI, and lifetime and current tobacco use as potential confounds was assessed first; no significant correlations were found between any of these variables and baseline telomerase activity or changes in telomerase activity with treatment, with the exception of a non-significant trend for a negative relationship between age and telomerase activity (r=−0.27, p=0.096), which was significant in the control group (r=−0.54, p<0.05), but not in the depressed group. There was a non-significant trend for gender to be related to telomerase activity (men greater than women) (r=0.40, p=0.098) in the control group but not in the overall sample or in the depressed subjects. To be conservative, all analyses reported here were controlled for both age and gender. Before analyzing the data, distributions were examined for normality, and non-normal distributions were natural log transformed (Ln).

Between-group comparison of the demographic variables was by independent sample t-tests, Chi square and independent sample Kruskal-Wallis tests. Other between-group data were analyzed by analysis of covariance (ANCOVA) when the covariates of age and gender covariates were applied, and paired t-tests were used for within-group comparisons. Correlations between variables were assessed by hierarchical linear regression, with age and sex entered as the first independent variables. Within-group correlations were by Pearson's or Spearman's correlation coefficients for normally and non-normally distributed data, respectively. All tests were 2-tailed with an alpha=0.05.

For purposes of characterizing response to antidepressant treatment, "Responders" were defined as subjects whose HDRS ratings improved by >50% relative to baseline, and "Non-responders" as those with lesser degrees of improvement.

Results

The depressed and control subjects did not significantly differ in age, gender distribution, ethnicity distribution, body-mass index, current and past alcohol or tobacco consumption, highest educational level attained and self-rated socioeconomic status (Adler N et al., $Health\ Psychol$, 19:586-592 (2000)), although mean household income was significantly higher in the controls than in the depressed subjects (p<0.005). Demographic characteristics of the subjects are provided in Table 2. The mean lifetime duration of depression in the depressed subjects was 170.6±143.0 months (median: 112.1 months; range: 9-426 months).

TABLE 2

Demographic Characteristics of Depressed and Control Subjects

| | Controls (n = 18) | Depressed (n = 20) | p |
|---|---|---|---|
| Age (Years) | 34.8 ± 9.6 | 37.0 ± 10.8 | ns |
| Gender (% Female) | 67 | 65 | ns |
| Ethnicity (% Caucasian, African-American, Hispanic, Asian) | 67, 17, 5, 11 | 70, 10, 10, 10 | ns |
| Body-Mass Index | 24.8 ± 3.9 | 26.2 ± 5.7 | ns |
| Used Tobacco Ever (%) | 53 | 35 | ns |
| Use Tobacco Currently (%) | 24 | 29 | ns |
| Alcohol Occasions per Month | 3.7 ± 4.5 | 4.9 ± 8.1 | ns |
| Alcohol Drinks per Occasion | 1.9 ± 1.1 | 1.5 ± 1.2 | ns |
| Subjective Socio-economic Status[1] | 6.50 ± 1.18 | 5.75 ± 1.60 | ns |
| Years of Education | 14.8 + 2.3 | 14.6 + 2.01 | ns |
| Household Income ($) | $72,000 ± 4,000 | $24,000 ± 9,000 | 0.005 |

[1]Subjective socioeconomic status was measured using a 10-rung ladder version of the MacArthur Scale of Subjective Social Status (Adler N et al., $Health\ Psychol$, 19: 586-592 (2000)).

Figure 4:
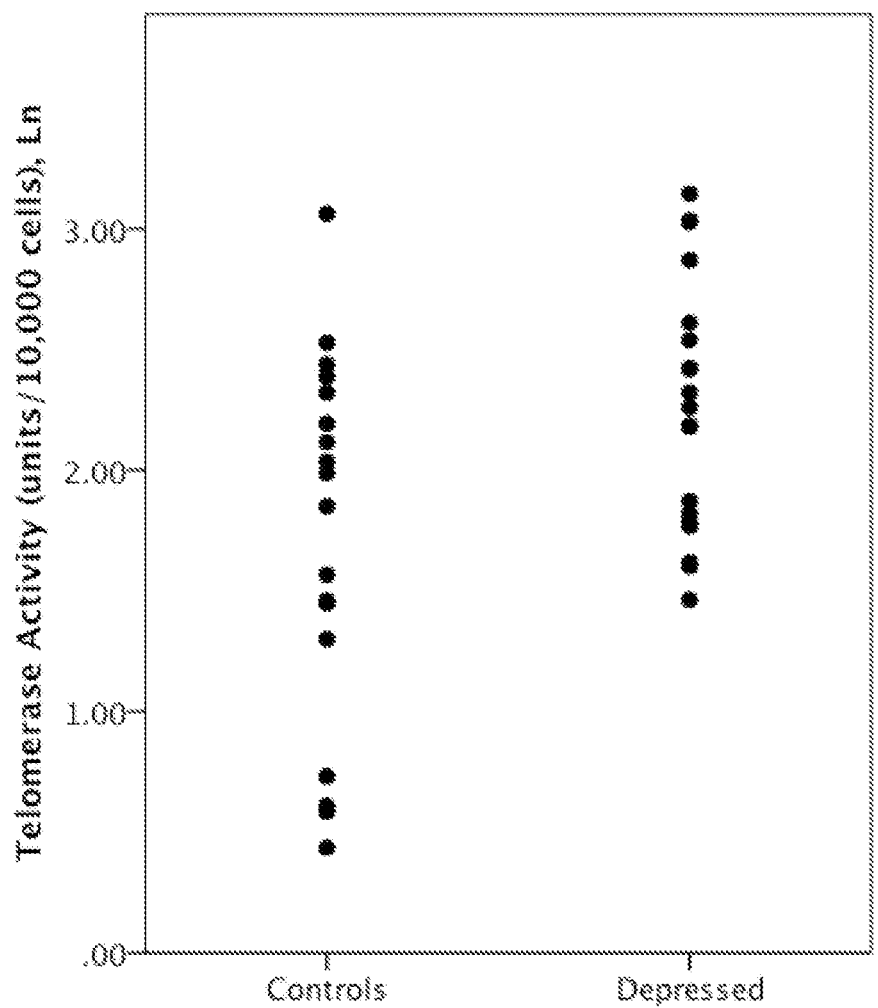
FIG. 4. Peripheral blood mononuclear cell (PBMC) telomerase activity (Ln) in un-medicated individuals with major depression vs. matched healthy controls. PBMC telomerase activity (Ln) is significantly higher in un-medicated depressed individuals compared to non-depressed healthy controls.
Figure 5:
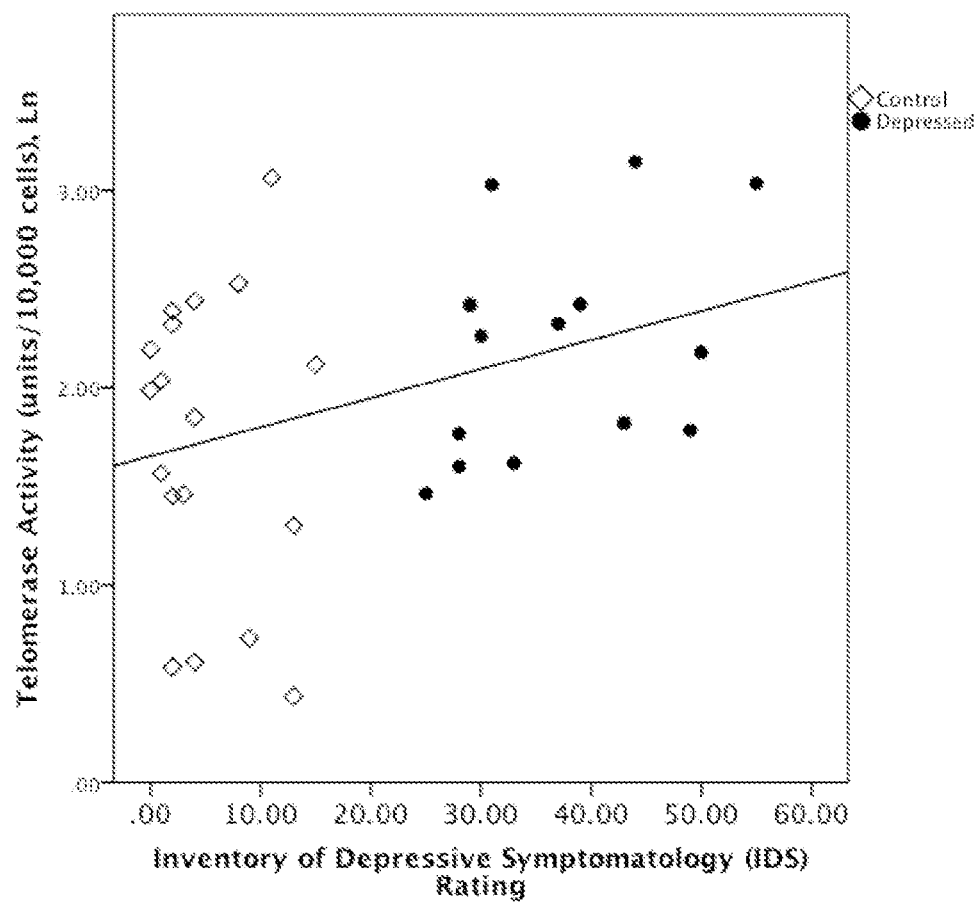
FIG. 5. Correlation between PBMC telomerase activity and depression. Correlation between PBMC telomerase activity (Ln) and ratings on the Inventory of Depressive Symptomatology (IDS) in un-medicated individuals with major depression and healthy controls.

Baseline PBMC telomerase activity was significantly higher in the depressed sample (n=20) (10.78±5.73 units/10,000 cells) than in the controls (n=18) (7.19±5.01 units/10,000 cells) (F=8.35, p=0.007) (FIG. 4). With depression considered as a continuous variable across groups, baseline PBMC telomerase activity was positively correlated with Inventory of Depressive Symptomatology ratings (r=0.36, p<0.05) (FIG. 5) and with Perceived Stress Scale ratings (r=0.36, p<0.05).

As expected, HDRS ratings significantly declined over the 8-week course of sertraline treatment (Mean±SD: Baseline: 18.50±3.65; Week 8: 10.19±4.62; paired t=5.67, p<0.000), representing changes ranging from 27% worsening to 82% improvement (mean improvement=42.3±31%). As a medication compliance check, plasma antidepressant levels were ascertained in the depressed subjects being treated with sertraline. The mean plasma concentration of [sertraline+N-desmethylsertraline] at Week 4 was 46.1±23.2 ng/ml; range: 10.0-97.0 ng/ml, and at Week 8 was 66.8±36.5 ng/ml; range: 10-146 ng/ml. All individuals had plasma concentrations that are within the range of published steady state concentrations for sertraline at therapeutic doses (Mauri M C et al., $Progress\ in\ neuro$-$psychopharmacology$ & $biological\ psychiatry$, 26(3):597-601 (2002)), indicating good compliance with medication treatment. There were no significant correlations between sertraline, N-desmethylsertraline, or the combined concentrations of [sertraline+N-desmethylsertraline] with either changes in HDRS ratings or changes in PBMC telomerase levels (p>0.30 in all cases).

Figure 6A:
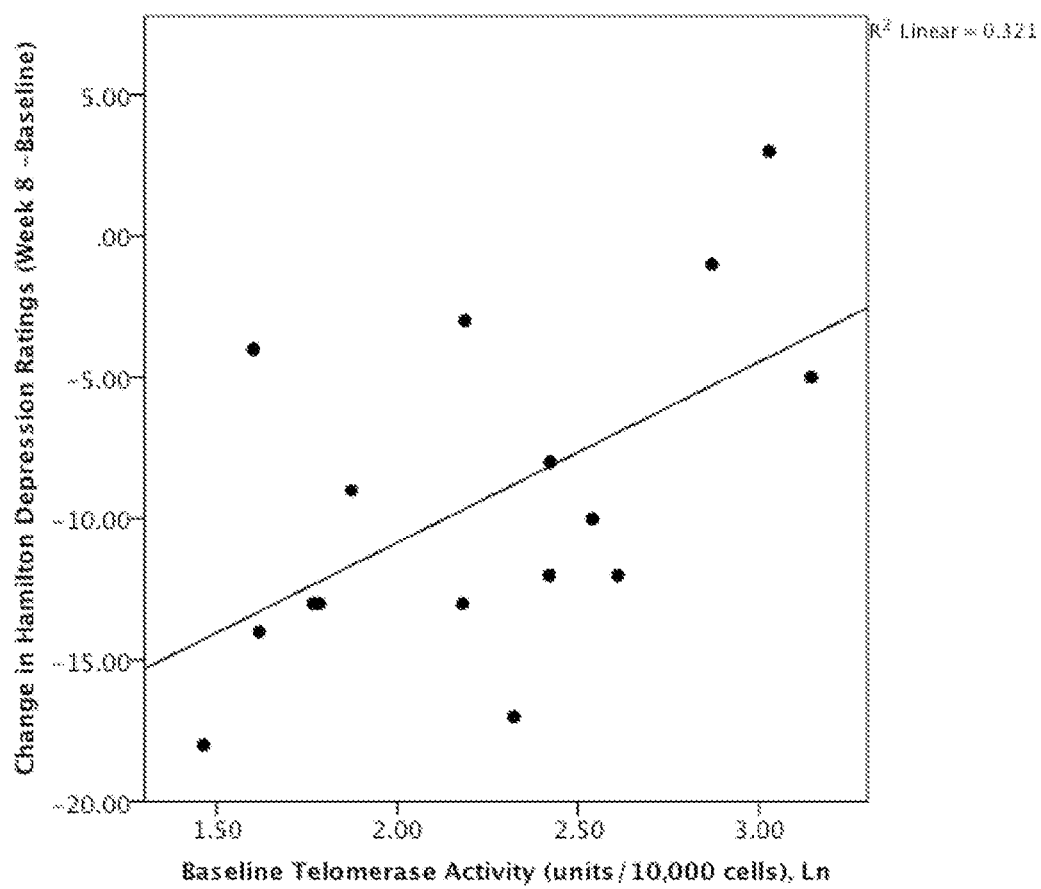
FIG. 6. Correlation between pre-treatment PBMC telomerase activity and treatment-associated changes in depression. A. Correlation between pre-treatment PBMC telomerase activity (Ln) and treatment-associated changes in depressed individuals in Hamilton Depression Rating Scale (HDRS) ratings. Treatment-associated changes are presented as the difference between HDRS ratings from before treatment to after 8 weeks of sertraline treatment. Increasingly negative numbers on the Y-axis indicate superior antidepressant responses. B. Correlation between pre-treatment PBMC telomerase activity (Ln) and Hamilton Depression Rating Scale (HDRS) ratings at the end of 8 weeks of sertraline treatment in depressed individuals. Lower numbers on the Y-axis indicate lesser ratings of depression. C. Correlation between pre-treatment PBMC telomerase activity (Ln) and percentage improvement in Hamilton Depression Rating Scale (HDRS) ratings in depressed individuals. Percentage improvement is calculated based on the difference between HDRS ratings from before treatment to after 8 weeks of sertraline treatment. Higher values on the Y-axis indicate greater percentage improvements in depression ratings.
Figure 6B:
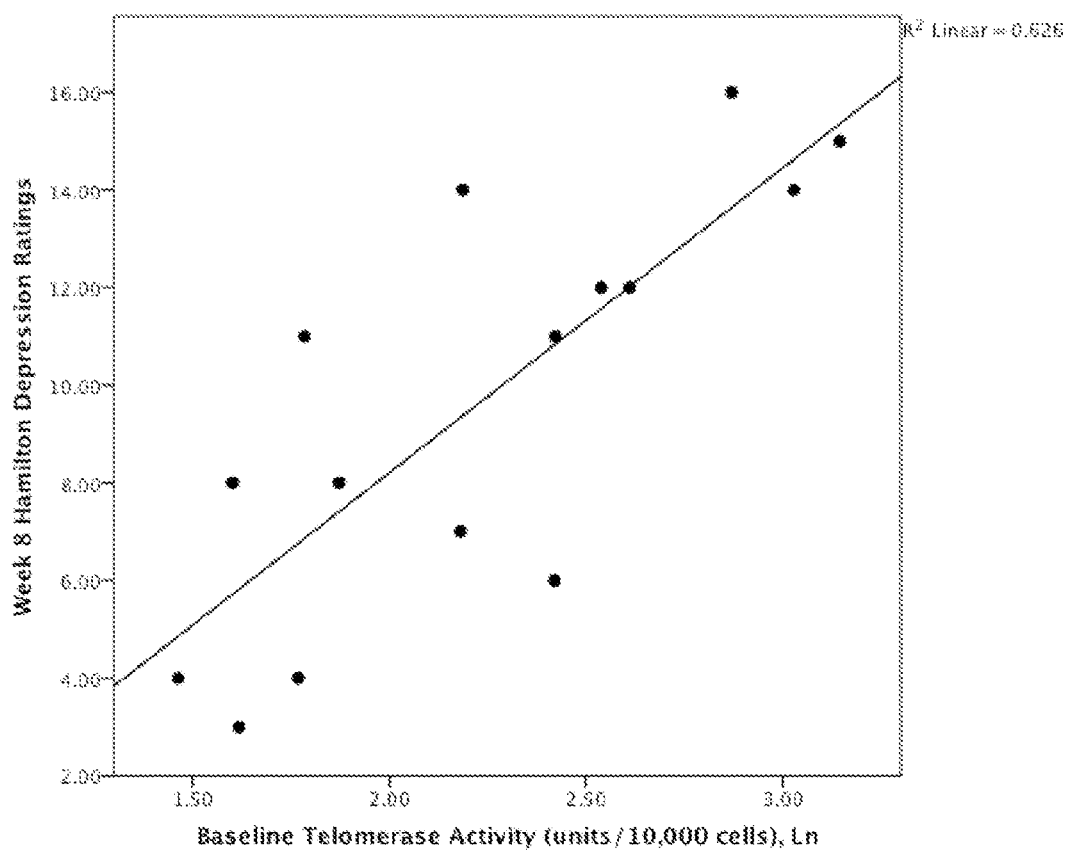
Figure 6C:
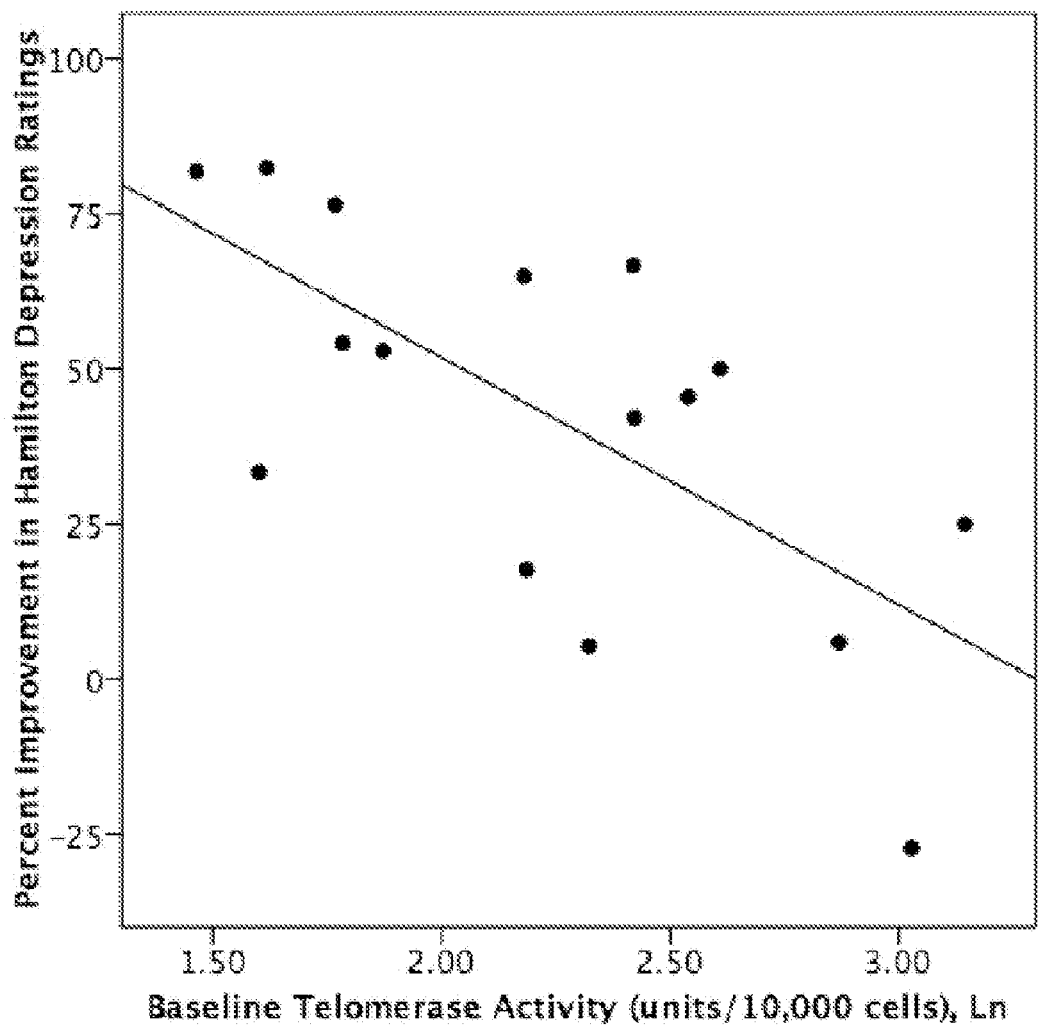

Within the depressed sample, baseline (pre-treatment) PBMC telomerase activity was directly correlated with changes in HDRS ratings over the course of treatment (Week 8 ratings minus Baseline ratings), whether considered as the absolute change in HDRS ratings (r=0.57, p<0.03) or as the percentage change in HDRS ratings (r=−0.74, p=0.002) (FIG. 6A-B). Baseline PBMC telomerase activity was also inversely correlated with absolute HDRS ratings at the end of treatment (Week 8) (r=0.80, p=0.001) (FIG. 6C). Specifically, lower baseline telomerase activity was associated with larger decreases (improvements) in HDRS ratings. When "Responders" and "Non-responders" were compared, the Responders had significantly lower baseline telomerase activity than Non-responders (Responders: 7.67+3.27 units/10,000 cells; Non-responders: 13.69+6.25 units/10,000 cells; F=8.51; p<0.02).

Figure 7:
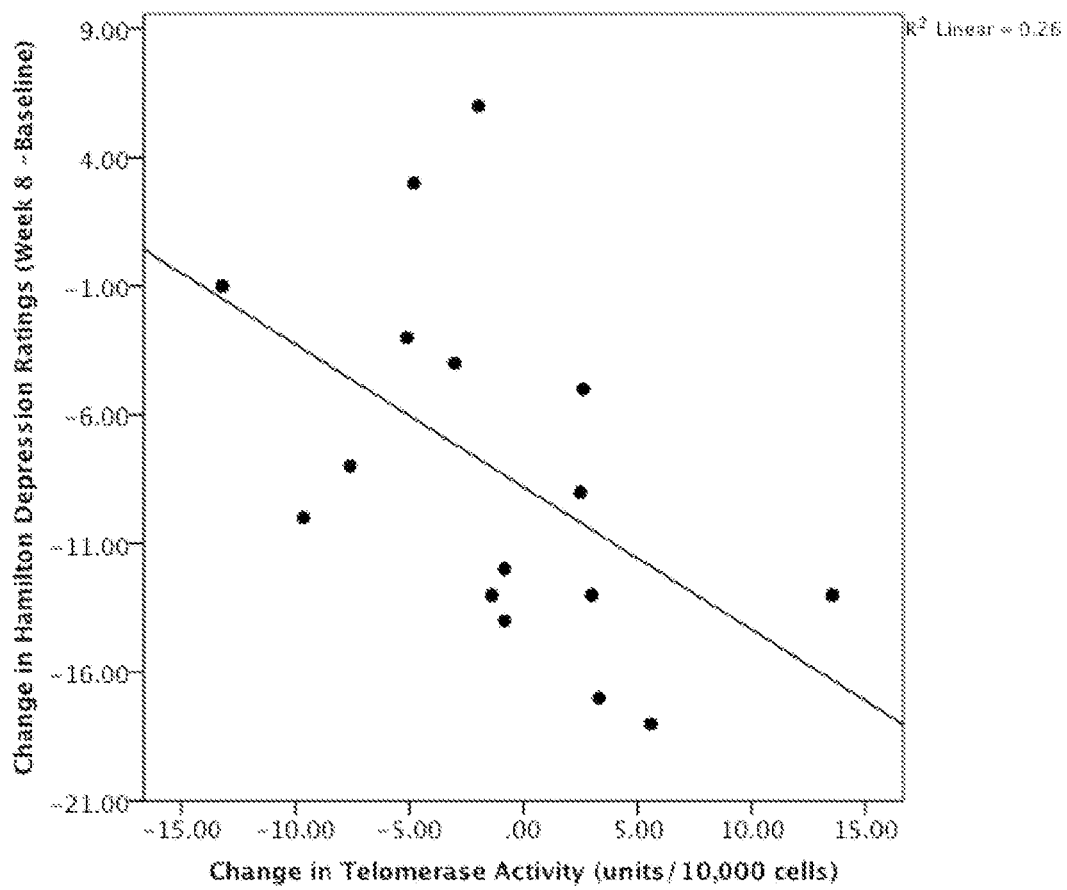
FIG. 7. Correlation between treatment-associated changes in PBMC telomerase activity and treatment-associated changes in Hamilton Depression Rating Scale (NDRS) ratings. Treatment consisted of 8 weeks of sertraline treatment. Higher numbers on the X-axis indicate greater increases in telomerase activity. Lower numbers on the Y-axis indicate superior antidepressant responses.

Average PBMC telomerase activity did not significantly change with antidepressant treatment across the whole group of depressed subjects (n=15) (Baseline: 10.51±6.10 units/10,000 cells; End of Week 8: 9.14+6.97 units/10,000 cells, paired t=0.75, ns). However, treatment-associated changes in PBMC telomerase activity (Week 8 ratings minus Baseline) were inversely correlated with changes in HDRS ratings (rs=−0.68, p=0.004) (FIG. 7). Specifically, greater treatment-associated increases in telomerase activity were associated with larger decreases (improvements) in HDRS ratings.

Discussion

PBMC telomerase activity was significantly higher in unmedicated depressed individuals compared to matched healthy controls. This finding was largely accounted for by those depressed individuals with relatively poor responses to 8-weeks of antidepressant treatment. Depressed individuals with greater antidepressant-associated increases in PBMC telomerase activity also had better antidepressant responses. Specifically, depressed individuals with relatively lower baseline (pre-medication) telomerase activities, and those whose telomerase activities increased the most with antidepressant treatment, showed the greatest benefit from antidepressant treatment.

The finding that PBMC telomerase activity is increased in depressed individuals was unexpected, since chronically depressed (Simon N M et al., $Biological\ psychiatry$, 60(5): 432-435 (2006); Lung F W et al., $Psychiatr\ Genet$, 17(3): 195-199 (2007); Wolkowitz O M et al., $Archives\ of\ general\ psychiatry$ 2010, in review) and stressed (Epel E S et al., $Proc.\ Natl.\ Acad.\ Sci.\ USA$, 101(49):17312-17315 (2004); Damjanovic A K et al., $J\ Immunol$, 179(6):4249-4254 (2007)) individuals have shorter leukocyte telomeres than matched controls, and since it was previously found that in chronically stressed (but generally not depressed) maternal caregivers have decreased PBMC telomerase activity (Epel E S et al., *Proceedings of the National Academy of Sciences of the United States of America*, 101(49):17312-17315 (2004)). However, this data is consistent with a number of other studies. For example, stressed caregivers of individuals with Alzheimer's disease were found to have shortened PBMC telomeres along with elevated telomerase activity (Damjanovic A K et al., *J Immunol*, 179(6):4249-4254 (2007)). Those authors interpreted their telomerase activity data as reflecting an "unsuccessful attempt to compensate for the excessive loss of telomeres" (Damjanovic A K et al., *J Immunol*, 179(6):4249-4254 (2007)). A variety of medical conditions are also characterized by significantly elevated telomerase activity in the face of significantly shortened telomeres. The possibility that increased telomerase activity reflects a compensatory response to cellular damage is consistent with preclinical data showing that telomerase preferentially elongates telomeres as their length declines (Hug N and Lingner J., *Chromosoma*, 115(6):413-425 (2006)), and with data that telomerase reverse transcriptase (TERT, the catalytic subunit of telomerase) is induced in response to certain types of cell injury, such as ischemic injury in brain cells (Kang H J et al., *J Neurosci*, 24(6): 1280-1287 (2004); Baek S et al., *Neuroscience letters*, 363(1):94-96 (2004)). Possible reasons for unsuccessful telomere repair by telomerase are not well-understood, but various explanations have been proposed (Calcagnile O and Gisselsson D, *Cytogenetic and genome research*, 118(2-4): 270-276 (2007)). It is also possible that elevated pro-inflammatory cytokines (Akiyama M et al., *Cancer Res*, 62(13):3876-3882 (2002); Akiyama M et al., *Cancer Res*, 63(1):18-21 (2003); Akiyama M et al., *Biochemical and biophysical research communications*, 316(2):528-532 (2004); Kawauchi K et al., *J Immunol*, 174(9):5261-5269 (2005)) and oxidative stress (Nishikawa T et al., *Liver Int* (2008)) that are seen in depression have direct stimulatory effects on telomerase activity, or that chronic stimulation of T lymphocytes leads top increased cell turnover, with an accompanying decrease in telomere length and increase in telomerase activity (Calado R T and Young N S, *N Engl J Med*, 361(24):2353-2365 (2009); Wu K et al., *J Immunol*, 165(8):4742-4747 (2000)). It is thus not known whether the increase in telomerase activity seen in depression marks a salutary process (attempted recovery of telomere length), a deleterious one (a direct stimulation by cytotoxic processes) or both. Lastly, we recently reported that PBMC telomerase activity significantly increased in response to acute psychological stress in caregivers and in healthy controls, and that, in the controls, the degree of telomerase activation was associated with perceptions of "threat" prior to and during the stress exposure (Epel E S et al., *Brain, behavior, and immunity* (2009)). It is unknown whether similar processes are called into play during chronic threat perceptions experienced by depressed individuals (Canli T et al., *Neuroreport*, 15(17):2585-2588 (2004); Kellough J L et al., *Behaviour research and therapy*, 46(11):1238-1243 (2008)), but these findings raise the possibility that acute changes contribute to the telomerase activation observed here.

The prediction of antidepressant response by PBMC telomerase activity, both prior to treatment and during treatment, has not previously been reported. One possible explanation of the finding that relatively low pre-treatment, but relatively high post-treatment telomerase activity levels predict better response to antidepressants involves the interaction of telomerase with inflammation and oxidative stress. Increased telomerase activity at baseline (pre-treatment) may be indicative of a more "toxic" cellular environment, e.g., more inflammation and oxidative stress, which itself predicts poorer response to antidepressants (Yoshimura R et al., *Progress in neuro-psychopharmacology & biological psychiatry*, 33(4):722-726 (2009); Khanzode S D et al., *Redox Rep*, 8(6):365-370 (2003)). In other words, the increased pre-treatment telomerase activity seen in the poor antidepressant responders may be a proxy (Effros R B, *The journals of gerontology*, 64(5):511-515 (2009)) rather than being directly involved in treatment response. It is also possible, however, that telomerase activation is, itself, beneficial, but that individuals with high pre-treatment telomerase activity may have sustained as much benefit as is possible, whereas those individuals who have normal or only mildly elevated telomerase activity at baseline may be the most likely to benefit from exogenous, medication-induced telomerase activation.

EXAMPLE 3

Telomere Length-To-Telomerase Ratio for Predicting Response to Treatment

This study characterized the ratio of leukocyte telomere length to PBMC telomerase activity in individuals with major depression compared to matched healthy controls, both before anti-depressant treatment and after 8 weeks of treatment, to determine whether the ratio would predict antidepressant response.

Figure 8:
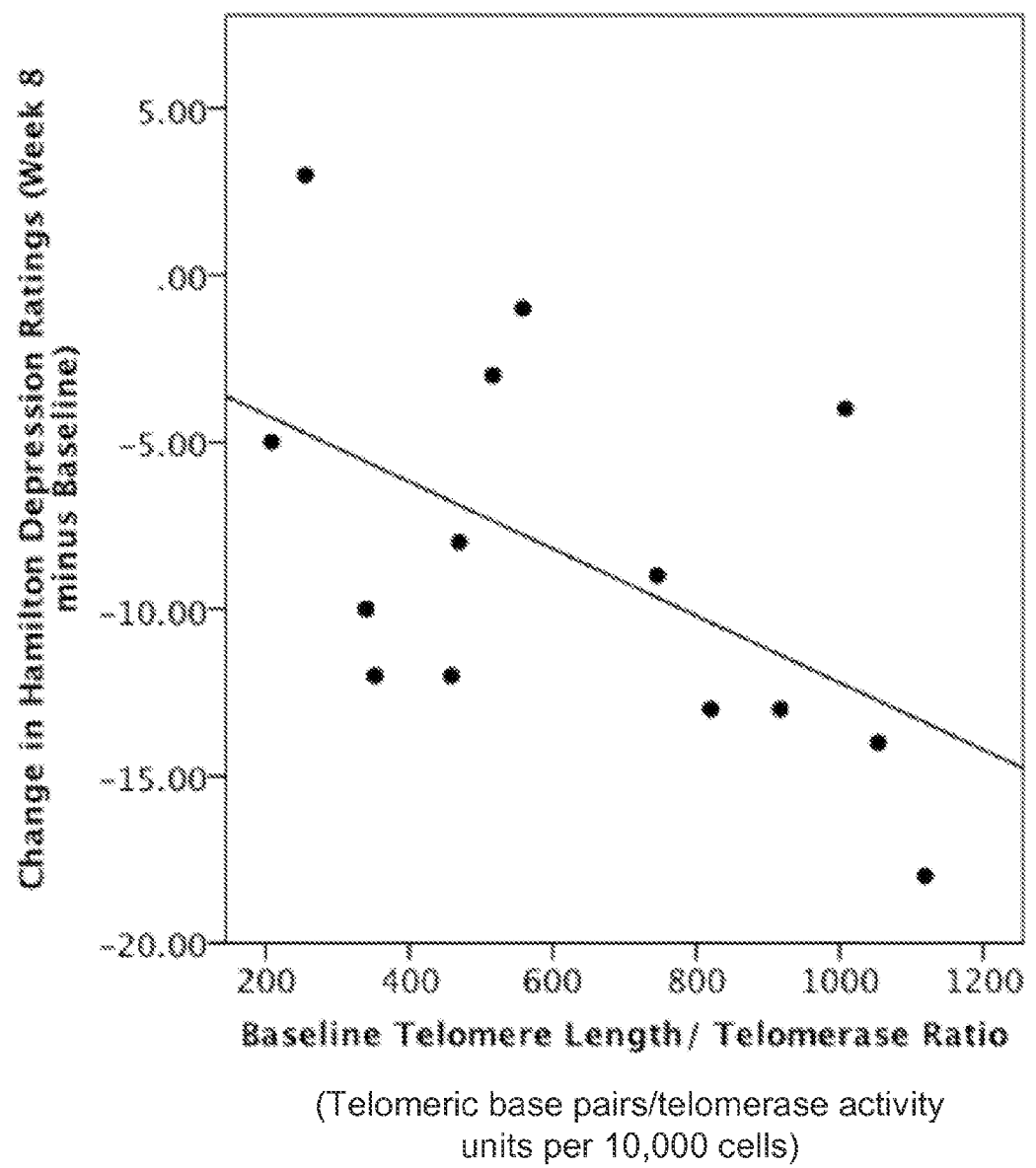
FIG. 8. Correlation between ratio of telomere length to telomerase activity and improvement in depression. Correlation between the ratio of telomere length to telomerase activity and treatment-associated changes in Hamilton Depression Rating Scale (HDRS) ratings in depressed individuals. The X-axis represents baseline ratio of telomere length to telomerase activity. The Y-axis represents absolute numerical change in depression ratings after 8 weeks of anti-depressant treatment with sertraline. Higher baseline telomere length to telomerase activity ratio is associated with a better anti-depressant response.

Using the methods described above in Examples 1 and 2 to measure telomere length and telomerase activity in individuals with major depression and healthy controls, a ratio of telomere length to telomerase activity was then calculated and plotted against treatment-associated changes in Hamilton Depression Rating Scale (HDRS) ratings after 8 weeks of anti-depressant treatment with sertraline. It was found that the telomere length-to-telomerase ratio predicts how well an individual will respond to anti-depressant treatment. As shown in FIG. 8, relatively higher pre-treatment telomere length-to-telomerase ratios predict a superior clinical response (raw change in HDRS ratings: r=0.55, p=0.064; percent change in HDRS ratings: r=0.64, p=0.025). Thus, pre-treatment telomerase activity, considered by itself or considered in ratio with telomere length, predicts anti-depressant treatment response.

EXAMPLE 4

Cell Aging Protection Score (CAPS) for Predicting Risk of Depression

The cell aging protection score (CAPS) incorporates both telomere length and telomerase activity. This study explored the possibility that CAPS could be used as a prognostic factor for predicting the risk of developing depression and/or predicting increases in depressive symptoms in two different samples of healthy women, a younger sample including maternal caregivers and controls, and an elderly sample including dementia caregivers and controls.

Procedure

Maternal caregivers and controls. A sample of healthy pre-menopausal women (some caregivers, some with healthy children) were divided into four CAPS groups: (1) short TL/low telomerase; (2) short TL/high telomerase; (3) long TL/low telomerase; and (4) long TL/high telomerase. The subjects were examined for differences in baseline depression, 18-month depression, and change in depression status (i.e., depressed to non-depressed; non-depressed to depressed; no change in status) from baseline to 18 months among the four groups. Age was covaried.

Dementia caregivers and controls. A sample of postmenopausal women (n=42, some caregivers for a relative with dementia) were divided into four CAPS groups: (1) short telomere length (TL)/low telomerase; (2) short TL/high telomerase; (3) long TL/low telomerase; and (4) long TL/high telomerase. The subjects were then examined for differences in baseline depression, 12-month depression, and change in depression status (i.e., depressed to non-depressed; non-depressed to depressed; no change in status) from baseline to 12 months among the four groups.

Results

For the group of maternal caregivers and controls, while TL and telomerase alone were not associated with depression at baseline, the combination of having a poor CAPS score (short TL and low telomerase) was marginally associated with depression, covarying for age; the mean score on the Center for Epidemiologic Studies Depression Scale (CESD) used here for likely depression was 15. Most of the women with poor CAPS were above 15, with a mean of 18. It was found that CAPS was associated with higher depression at baseline, marginally significant (p=0.07, 1-tailed). This finding in healthy women was somewhat distinct from what was found in patients with MDD described above, in whom depression was associated with higher telomerase activity. This likely reflects a state change that accompanies the development of major depression, such that increases in telomerase activity represent an unsuccessful attempt to delay telomere shortening.

Figure 9A:
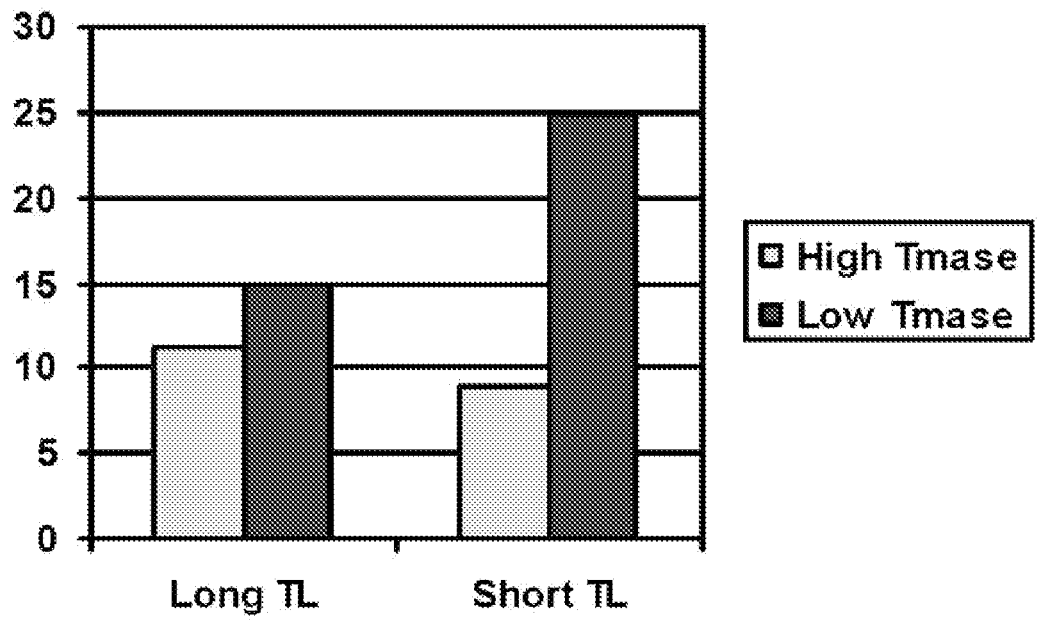
FIG. 9. Cell aging protection score (CAPS) for predicting depression. A. CAPS group is correlated with extent of depressive symptoms among caregiver and control females eighteen months after baseline. To derive CAPS groupings, subjects were divided into four CAPS groups: (1) short telomere length (TL), low telomerase; (2) short TL, high telomerase; (3) long TL, low telomerase; and (4) long TL, high telomerase. Incidence of depression at baseline was then assessed for each CAPS group. Eighteen months after baseline, there was a significant association between greater depressive symptoms (y axis) and a poor baseline CAPS score (short TL, low telomerase). B. CAPS group is correlated with incidence of depression among caregiver and control females twelve months after baseline. Subjects were divided into four CAPS groups as described in (A). Incidence of depression at baseline and 12 months later was then assessed for each CAPS group. Twelve months after baseline, there was a trend towards more depression in subjects with a poor baseline CAPS score (short TL, low telomerase).

Additionally, the long-term prognostic value of CAPS was evaluated in maternal caregivers. When these same subjects were evaluated for depression 1.5 years after baseline, it was found that the baseline CAPS score was still important. Covarying for age, women with low telomerase at baseline showed a significantly greater depression score at 1.5 years, F (4,32)=5.4, p=0.03. Even when controlling for baseline depression, it was found that low telomerase alone was still a significant predictor of increase in depressive symptoms over the 1.5 year (p=0.02, 1-tailed). Further, when examining CAPS groups, poor CAPS (the combination of having short TL and low telomerase) was associated with greater depressive symptoms at 1.5 years, although marginally significant due to reduced sample size (F=2.5, p=0.07, 1-tailed) (FIG. 9A).

Figure 9B:
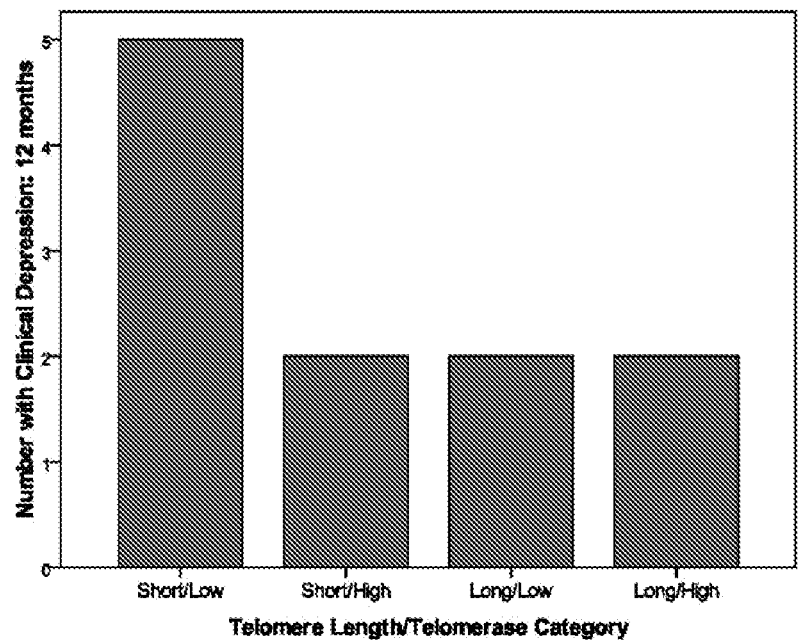

For the group of dementia caregivers and controls, there were no significant group differences in relative telomere length and/or telomerase activity and incidence of depression at baseline. Women with short TL did have the highest incidence of depression, but the difference was non-significant. At 12 months, there was a distinct trend towards more depression in those subjects with poor baseline CAPS—short TL and low telomerase—compared with those with short TL and high telomerase (Pearson's Chi Square=2.61, p=0.05; Likelihood Ratio=2.65, 1-tailed) (FIG. 9B). Further analyses revealed significant differences between groups in the change in depression status variable. Specifically, among those with short TL, high telomerase was associated with a greater probability of changing from depressed to non-depressed during the year (p=0.04). These findings are consistent with the proposition that relatively higher telomerase activity has salutary or protective effects in depression, even in the presence of shortened telomeres. This is also consistent with the above-described examples that successful anti-depressant treatments are accompanied by significant increases in telomerase activity. Together, these two studies suggest that telomerase alone and/or CAPS score are helpful predictors of risk for depressive symptoms in a high risk sample over at least one year.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of detecting a ratio of telomere length to telomerase activity in a subject, the method comprising the steps of:
   (a) obtaining from the subject a sample comprising peripheral blood mononuclear cells or leukocytes, wherein the subject is an individual who has been clinically diagnosed with Major Depressive Disorder,
   (b) detecting a ratio of telomere length to telomerase activity in the sample from the subject that is higher than a ratio of telomere length to telomerase activity detected for a healthy control subject, wherein the detecting comprises measuring telomere length and telomerase activity and wherein the measuring comprises:
       (i) quantifying telomere length by quantitative PCR; and
       (ii) quantifying telomerase activity by telomeric repeat amplification protocol (TRAP) visualized by gel electrophoresis and phosphorimager detection; and
   (c) administering an anti-depressant treatment to the subject, wherein the anti-depressant treatment is anti-depressant medication.

2. The method of any of claims 1, wherein the anti-depressant treatment comprises administering anti-depressant medication for at least 8 weeks.

3. The method of claim 1, comprising detecting an amount of telomerase activity in the sample from the subject that is lower than 9.5 units/10,000 cells.

4. The method of claim 1, wherein the anti-depressant medication is a selective serotonin reuptake inhibitor.

5. The method of claim 1, wherein the sample comprises peripheral blood mononuclear cells.

6. The method of claim 1, wherein the sample comprises leukocytes.

7. The method of claim 1, wherein the subject is clinically diagnosed with Major Depressive Disorder using a Structural Clinical Interview for DSM-IV(SCID).

* * * * *